(12) United States Patent
Conlon et al.

(10) Patent No.: US 7,850,712 B2
(45) Date of Patent: Dec. 14, 2010

(54) SELF-SHIELDING SUTURE ANCHOR

(75) Inventors: Sean P. Conlon, Loveland, OH (US); Duane A. Linenkugel, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 11/274,352

(22) Filed: Nov. 15, 2005

(65) Prior Publication Data

US 2007/0112383 A1    May 17, 2007

(51) Int. Cl.
*A61B 17/04* (2006.01)
(52) U.S. Cl. .................................... 606/232
(58) Field of Classification Search ............ 606/72, 606/73, 232, 139, 148; 24/291, 292, 115 G
See application file for complete search history.

(56) References Cited

U.S. PATENT DOCUMENTS

| | | | |
|---|---|---|---|
| 1,153,450 A | 9/1915 | Schaff | |
| 2,069,878 A | 2/1937 | Flood | |
| 3,215,027 A * | 11/1965 | Modrey et al. | 411/76 |
| 3,470,834 A | 10/1969 | Bone | |
| 3,692,029 A | 9/1972 | Adair | |
| 3,890,970 A | 6/1975 | Gullen | |
| 3,990,619 A | 11/1976 | Russell | |
| 4,006,747 A | 2/1977 | Kronenthal et al. | |
| 4,022,191 A | 5/1977 | Jamshidi | |
| 4,235,238 A | 11/1980 | Ogiu et al. | |
| 4,275,717 A | 6/1981 | Bolesky | |
| 4,393,872 A | 7/1983 | Reznik et al. | |
| 4,616,650 A * | 10/1986 | Green et al. | 606/143 |
| 4,669,473 A | 6/1987 | Richards et al. | |
| 4,705,040 A | 11/1987 | Mueller et al. | |
| 4,741,330 A | 5/1988 | Hayhurst | |
| 4,790,304 A | 12/1988 | Rosenberg | |
| 4,851,005 A | 7/1989 | Hunt et al. | |
| 4,869,259 A | 9/1989 | Elkins | |
| 4,901,721 A * | 2/1990 | Hakki | 606/103 |
| 5,037,422 A | 8/1991 | Hayhurst et al. | |
| 5,041,129 A * | 8/1991 | Hayhurst et al. | 606/232 |
| 5,046,513 A | 9/1991 | Gatturna et al. | |
| 5,053,046 A | 10/1991 | Janese | |

(Continued)

FOREIGN PATENT DOCUMENTS

EP    0797957    10/1997

(Continued)

OTHER PUBLICATIONS

US, Office Action, U.S. Appl. No. 11/274,354 (May 7, 2007).

(Continued)

*Primary Examiner*—Darwin P Erezo
*Assistant Examiner*—Dianne Dornbusch

(57) ABSTRACT

A self-shielding suture anchor is provided and includes a body having a proximal end and a distal end, the distal end including a penetrating tip. The suture anchor also includes a shielding element movable relative to the distal end between a shielding position, wherein the shielding element is distal to the penetrating tip, and a retracted position, wherein the shielding element is proximal to the penetrating tip. The suture anchor also includes a spring element operatively connected to the shielding element to bias the shielding element to the shielding position.

17 Claims, 16 Drawing Sheets

U.S. PATENT DOCUMENTS

| | | | |
|---|---|---|---|
| 5,080,543 A | 1/1992 | Murphy | |
| 5,080,663 A | 1/1992 | Mills et al. | |
| 5,081,997 A | 1/1992 | Bosley, Jr. et al. | |
| 5,084,050 A | 1/1992 | Draenert | |
| 5,104,382 A * | 4/1992 | Brinkerhoff et al. | 604/164.12 |
| 5,123,914 A | 6/1992 | Cope | |
| 5,197,971 A | 3/1993 | Bonutti | |
| 5,217,486 A | 6/1993 | Rice et al. | |
| 5,258,015 A | 11/1993 | Li et al. | |
| 5,269,809 A | 12/1993 | Hayhurst et al. | |
| 5,282,832 A | 2/1994 | Toso et al. | |
| 5,312,435 A | 5/1994 | Nash et al. | |
| 5,370,662 A * | 12/1994 | Stone et al. | 606/232 |
| 5,383,905 A | 1/1995 | Golds et al. | |
| 5,405,354 A | 4/1995 | Sarrett | |
| 5,423,760 A * | 6/1995 | Yoon | 604/164.11 |
| 5,464,425 A | 11/1995 | Skiba | |
| 5,470,337 A * | 11/1995 | Moss | 606/139 |
| 5,480,403 A | 1/1996 | Lee et al. | |
| 5,486,197 A * | 1/1996 | Le et al. | 606/232 |
| 5,514,159 A | 5/1996 | Matula et al. | |
| 5,527,342 A | 6/1996 | Pietrzak et al. | |
| 5,549,630 A | 8/1996 | Bonutti | |
| 5,584,861 A | 12/1996 | Swain et al. | |
| 5,584,862 A | 12/1996 | Bonutti | |
| 5,591,206 A | 1/1997 | Moufarrege | |
| 5,593,422 A | 1/1997 | Muijs Van de Moer et al. | |
| 5,601,557 A | 2/1997 | Hayhurst | |
| 5,626,614 A | 5/1997 | Hart | |
| 5,630,824 A | 5/1997 | Hart | |
| 5,643,253 A | 7/1997 | Baxter et al. | |
| 5,643,321 A | 7/1997 | McDevitt | |
| 5,645,589 A | 7/1997 | Li | |
| 5,647,874 A * | 7/1997 | Hayhurst | 606/72 |
| 5,649,963 A | 7/1997 | McDevitt | |
| 5,662,683 A | 9/1997 | Kay | |
| 5,667,509 A * | 9/1997 | Westin | 606/80 |
| 5,681,351 A | 10/1997 | Jamiolkowski et al. | |
| 5,707,395 A | 1/1998 | Li | |
| 5,728,114 A | 3/1998 | Evans et al. | |
| 5,728,136 A | 3/1998 | Thal | |
| 5,733,306 A | 3/1998 | Bonutti | |
| 5,755,730 A | 5/1998 | Swain et al. | |
| 5,782,864 A | 7/1998 | Lizardi | |
| 5,792,153 A | 8/1998 | Swain et al. | |
| 5,800,445 A | 9/1998 | Ratcliff et al. | |
| 5,807,403 A | 9/1998 | Beyar et al. | |
| 5,814,071 A | 9/1998 | McDevitt et al. | |
| 5,836,314 A | 11/1998 | Benderev et al. | |
| 5,891,168 A | 4/1999 | Thal | |
| 5,893,856 A | 4/1999 | Jacob et al. | |
| 5,899,921 A | 5/1999 | Caspari et al. | |
| 5,902,321 A | 5/1999 | Caspari et al. | |
| 5,904,696 A | 5/1999 | Rosenman | |
| 5,916,236 A | 6/1999 | Muijs Van de Moer et al. | |
| RE36,289 E | 8/1999 | Le et al. | |
| 5,931,844 A | 8/1999 | Thompson et al. | |
| 5,935,129 A | 8/1999 | McDevitt et al. | |
| 5,941,900 A | 8/1999 | Bonutti | |
| 5,948,000 A | 9/1999 | Larsen et al. | |
| 5,954,747 A | 9/1999 | Clark | |
| 5,957,953 A | 9/1999 | DiPoto et al. | |
| 6,036,694 A | 3/2000 | Goble et al. | |
| 6,036,701 A | 3/2000 | Rosenman | |
| 6,066,146 A | 5/2000 | Carroll et al. | |
| 6,068,648 A | 5/2000 | Cole et al. | |
| 6,086,608 A | 7/2000 | Ek et al. | |
| 6,126,670 A | 10/2000 | Walker et al. | |
| RE36,974 E | 11/2000 | Bonutti | |
| 6,146,406 A | 11/2000 | Shluzas et al. | |
| 6,149,669 A | 11/2000 | Li | |
| 6,152,935 A | 11/2000 | Kammerer et al. | |
| 6,200,329 B1 | 3/2001 | Fung et al. | |
| 6,214,031 B1 * | 4/2001 | Schmieding et al. | 606/232 |
| 6,245,080 B1 | 6/2001 | Levinson | |
| 6,264,677 B1 * | 7/2001 | Simon et al. | 606/232 |
| 6,287,325 B1 | 9/2001 | Bonutti | |
| 6,306,163 B1 | 10/2001 | Fitz | |
| 6,319,263 B1 | 11/2001 | Levinson | |
| 6,332,885 B1 | 12/2001 | Martella | |
| 6,338,738 B1 * | 1/2002 | Bellotti et al. | 606/232 |
| 6,387,114 B2 | 5/2002 | Adams | |
| 6,436,099 B1 | 8/2002 | Drewry et al. | |
| 6,447,524 B1 | 9/2002 | Knodel et al. | |
| 6,500,184 B1 | 12/2002 | Chan et al. | |
| 6,500,195 B2 | 12/2002 | Bonutti | |
| 6,506,190 B1 | 1/2003 | Walshe | |
| 6,524,328 B2 | 2/2003 | Levinson | |
| 6,527,794 B1 | 3/2003 | McDevitt et al. | |
| 6,561,969 B2 | 5/2003 | Frazier et al. | |
| 6,569,167 B1 | 5/2003 | Bobechko et al. | |
| 6,575,984 B2 | 6/2003 | Beyar | |
| 6,575,987 B2 | 6/2003 | Gellman et al. | |
| 6,575,998 B2 | 6/2003 | Beyar | |
| 6,613,070 B2 | 9/2003 | Redmond et al. | |
| 6,626,899 B2 | 9/2003 | Houser et al. | |
| 6,638,279 B2 | 10/2003 | Bonutti | |
| 6,652,561 B1 | 11/2003 | Tran | |
| 6,652,562 B2 | 11/2003 | Collier et al. | |
| 6,660,023 B2 | 12/2003 | McDevitt et al. | |
| 6,663,639 B1 | 12/2003 | Laufer et al. | |
| 6,689,153 B1 | 2/2004 | Skiba | |
| 6,692,516 B2 | 2/2004 | West, Jr. et al. | |
| 6,699,263 B2 | 3/2004 | Cope | |
| 6,712,804 B2 | 3/2004 | Roue et al. | |
| 6,730,110 B1 | 5/2004 | Harari et al. | |
| 6,730,112 B2 | 5/2004 | Levinson | |
| 6,746,472 B2 | 6/2004 | Frazier et al. | |
| 6,749,620 B2 * | 6/2004 | Bartlett | 606/202 |
| 6,821,285 B2 | 11/2004 | Laufer et al. | |
| 6,846,313 B1 | 1/2005 | Rogers et al. | |
| 6,860,895 B1 | 3/2005 | Akerfeldt et al. | |
| 7,115,136 B2 | 10/2006 | Park et al. | |
| 7,144,414 B2 | 12/2006 | Harvie et al. | |
| 7,150,750 B2 | 12/2006 | Damarati | |
| 7,341,558 B2 * | 3/2008 | de la Torre et al. | 600/204 |
| 7,390,329 B2 | 6/2008 | Westra et al. | |
| 7,651,509 B2 | 1/2010 | Bojarski et al. | |
| 2001/0010008 A1 * | 7/2001 | Gellman et al. | 606/232 |
| 2002/0059938 A1 | 5/2002 | Fogarty et al. | |
| 2002/0077631 A1 | 6/2002 | Lubbers et al. | |
| 2002/0082622 A1 | 6/2002 | Kane | |
| 2002/0111653 A1 | 8/2002 | Foerster | |
| 2002/0128684 A1 | 9/2002 | Foerster | |
| 2002/0161382 A1 | 10/2002 | Neisz et al. | |
| 2003/0018358 A1 | 1/2003 | Saadat | |
| 2003/0023268 A1 | 1/2003 | Lizardi | |
| 2003/0093117 A1 | 5/2003 | Saadat | |
| 2003/0097150 A1 | 5/2003 | Fallin et al. | |
| 2003/0109900 A1 | 6/2003 | Martinek | |
| 2003/0144694 A1 | 7/2003 | Chanduszko et al. | |
| 2003/0158581 A1 | 8/2003 | Levinson | |
| 2003/0163143 A1 | 8/2003 | Wakabayashi | |
| 2003/0163160 A1 | 8/2003 | O'Malley et al. | |
| 2003/0171760 A1 | 9/2003 | Gambale | |
| 2003/0191497 A1 | 10/2003 | Cope | |
| 2003/0208233 A1 | 11/2003 | Bobechko et al. | |
| 2004/0049194 A1 | 3/2004 | Harvie et al. | |
| 2004/0049211 A1 | 3/2004 | Tremulis et al. | |
| 2004/0092969 A1 | 5/2004 | Kumar | |
| 2004/0093023 A1 | 5/2004 | Allen et al. | |
| 2004/0098050 A1 * | 5/2004 | Foerster et al. | 606/232 |
| 2004/0116949 A1 | 6/2004 | Ewers et al. | |
| 2004/0122456 A1 | 6/2004 | Saadat et al. | |

| | | |
|---|---|---|
| 2004/0122473 A1 | 6/2004 | Ewers et al. |
| 2004/0133238 A1 | 7/2004 | Cerier |
| 2004/0138707 A1 | 7/2004 | Greenhalgh |
| 2004/0147958 A1 | 7/2004 | Lam et al. |
| 2004/0186514 A1 | 9/2004 | Swain et al. |
| 2004/0186566 A1 | 9/2004 | Hindrichs et al. |
| 2004/0193215 A1 | 9/2004 | Harari et al. |
| 2004/0225305 A1 | 11/2004 | Ewers et al. |
| 2004/0230095 A1 | 11/2004 | Stefanchik et al. |
| 2004/0249392 A1 | 12/2004 | Mikkaichi et al. |
| 2004/0260344 A1 | 12/2004 | Lyons et al. |
| 2005/0033319 A1 | 2/2005 | Gambale et al. |
| 2005/0055052 A1 | 3/2005 | Lombardo et al. |
| 2005/0075654 A1 | 4/2005 | Kelleher |
| 2005/0113851 A1 | 5/2005 | Swain et al. |
| 2005/0143762 A1 | 6/2005 | Paraschac et al. |
| 2005/0149115 A1 | 7/2005 | Roue et al. |
| 2005/0187567 A1 | 8/2005 | Baker et al. |
| 2005/0192599 A1 | 9/2005 | Demarais |
| 2005/0228415 A1 | 10/2005 | Gertner |
| 2005/0234512 A1 | 10/2005 | Nakao |
| 2005/0245945 A1 | 11/2005 | Ewers et al. |
| 2005/0250984 A1 | 11/2005 | Lam et al. |
| 2005/0250985 A1 | 11/2005 | Saadat et al. |
| 2005/0250986 A1 | 11/2005 | Rothe et al. |
| 2005/0250987 A1 | 11/2005 | Ewers et al. |
| 2005/0250988 A1 | 11/2005 | Ewers et al. |
| 2005/0251157 A1 | 11/2005 | Saadat et al. |
| 2005/0251159 A1 | 11/2005 | Ewers et al. |
| 2005/0251160 A1 | 11/2005 | Saadat et al. |
| 2005/0251161 A1 | 11/2005 | Saadat et al. |
| 2005/0251162 A1 | 11/2005 | Rothe et al. |
| 2005/0251189 A1 | 11/2005 | Saadat et al. |
| 2005/0251202 A1 | 11/2005 | Ewers et al. |
| 2005/0251205 A1 | 11/2005 | Ewers et al. |
| 2005/0251206 A1 | 11/2005 | Maahs et al. |
| 2005/0251207 A1 | 11/2005 | Flores et al. |
| 2005/0251208 A1 | 11/2005 | Elmer et al. |
| 2005/0251209 A1 | 11/2005 | Saadat et al. |
| 2005/0251210 A1 | 11/2005 | Westra et al. |
| 2005/0256531 A9 | 11/2005 | Bolduc et al. |
| 2005/0261708 A1 | 11/2005 | Pasricha et al. |
| 2005/0261709 A1 | 11/2005 | Sakamoto et al. |
| 2005/0261710 A1 | 11/2005 | Sakamoto et al. |
| 2006/0030884 A1 | 2/2006 | Yeung et al. |
| 2006/0229669 A1 | 10/2006 | Mirizzi et al. |
| 2007/0049970 A1 | 3/2007 | Belef et al. |
| 2007/0112384 A1 | 5/2007 | Conlon et al. |
| 2007/0112385 A1 | 5/2007 | Conlon |

FOREIGN PATENT DOCUMENTS

| | | |
|---|---|---|
| EP | 0634142 | 3/1998 |
| EP | 0838197 | 4/1998 |
| EP | 0751745 | 5/1999 |
| EP | 0768837 | 5/2000 |
| EP | 0643945 | 3/2002 |
| EP | 0835642 | 8/2002 |
| EP | 0834281 | 3/2003 |
| EP | 0847727 | 2/2004 |
| EP | 1386585 | 2/2004 |
| EP | 1202672 | 3/2004 |
| EP | 1447052 | 8/2004 |
| EP | 1346699 | 1/2005 |
| GB | 1549666 | 4/1976 |
| JP | 2004160255 | 6/2004 |
| WO | 92/04870 | 4/1992 |
| WO | 9900058 | 1/1999 |
| WO | 00/57796 | 10/2000 |
| WO | 00/61012 | 10/2000 |
| WO | 01/10312 | 2/2001 |
| WO | 01/66001 | 9/2001 |
| WO | 01/66018 | 9/2001 |
| WO | 01/89393 | 11/2001 |
| WO | 02/30293 | 4/2002 |
| WO | 02/094108 | 11/2002 |
| WO | 03/065904 | 8/2003 |
| WO | 03/077772 | 9/2003 |
| WO | 03/096910 | 11/2003 |
| WO | 2004/024006 | 3/2004 |
| WO | 2005/034729 | 4/2005 |
| WO | 2005/099591 | 10/2005 |
| WO | 2005/110244 | 11/2005 |

OTHER PUBLICATIONS

US, Final Office Action, U.S. Appl. No. 11/274,354 (Oct. 30, 2007).
US, Advisory Action, U.S. Appl. No. 11/274,354 (Dec. 27, 2007).
US, Office Action, U.S. Appl. No. 11/274,354 (Apr. 4, 2008).
US, Final Office Action, U.S. Appl. No. 11/274,354 (Jan. 13, 2009).
US, Advisory Action, U.S. Appl. No. 11/274,354 (Mar. 24, 2009).
US, Office Action, U.S. Appl. No. 11/274,354 (Jun. 4, 2009).
US, Interview Summary, U.S. Appl. No. 11/274,354 (Aug. 28, 2009).
US, Office Action, U.S. Appl. No. 11/274,354 (Nov. 24, 2009).
US, Notice of Allowance, U.S. Appl. No. 11/274,354 (Mar. 22, 2010).
US, Notice of Allowance, U.S. Appl. No. 11/274,354 (Jun. 17, 2010).
US, Office Action, U.S. Appl. No. 11/274,358 (Feb. 5, 2008).
US, Final Office Action, U.S. Appl. No. 11/274,358 (May 21, 2008).
US, Advisory Action, U.S. Appl. No. 11/274,358 (Jul. 29, 2008).
US, Office Action, U.S. Appl. No. 11/274,358 (Sep. 16, 2008).
US, Office Action, U.S. Appl. No. 11/274,358 (Feb. 3, 2009).
US, Final Office Action, U.S. Appl. No. 11/274,358 (Aug. 6, 2009).
US, Advisory Action, U.S. Appl. No. 11/274,358 (Oct. 19, 2009).
US, Office Action, U.S. Appl. No. 11/274,358 (Feb. 2, 2010).
US, Office Action, U.S. Appl. No. 11/274,358 (Jul. 12, 2010).
US 5,656,614, 05/1997, Hart (withdrawn)*

* cited by examiner

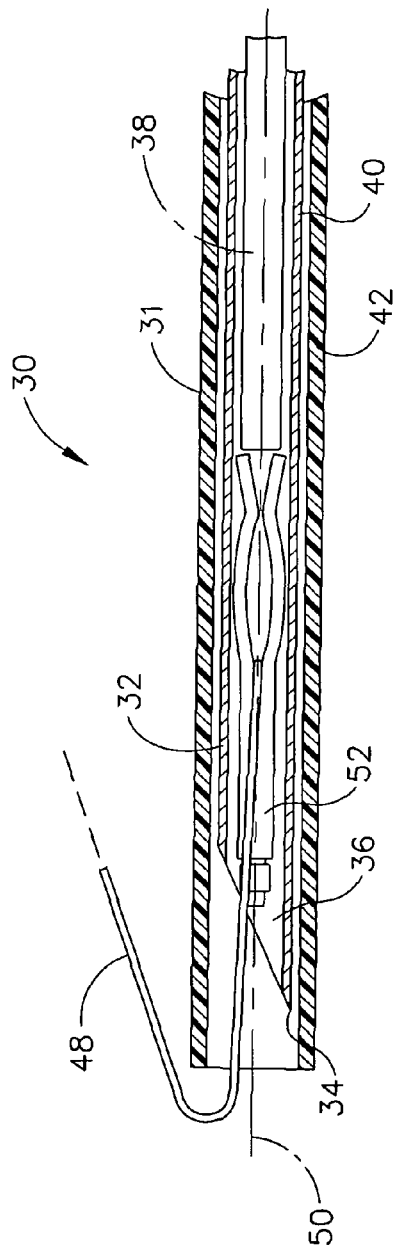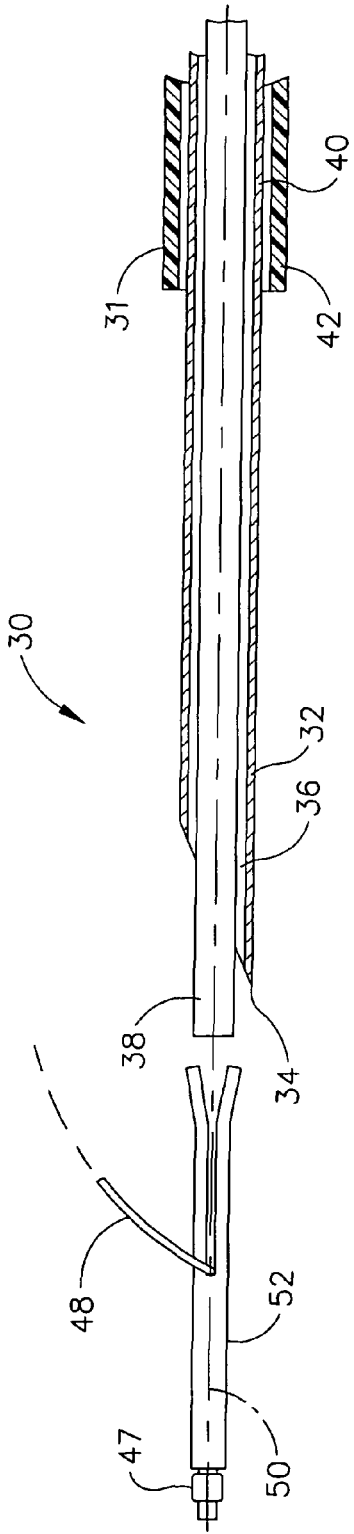

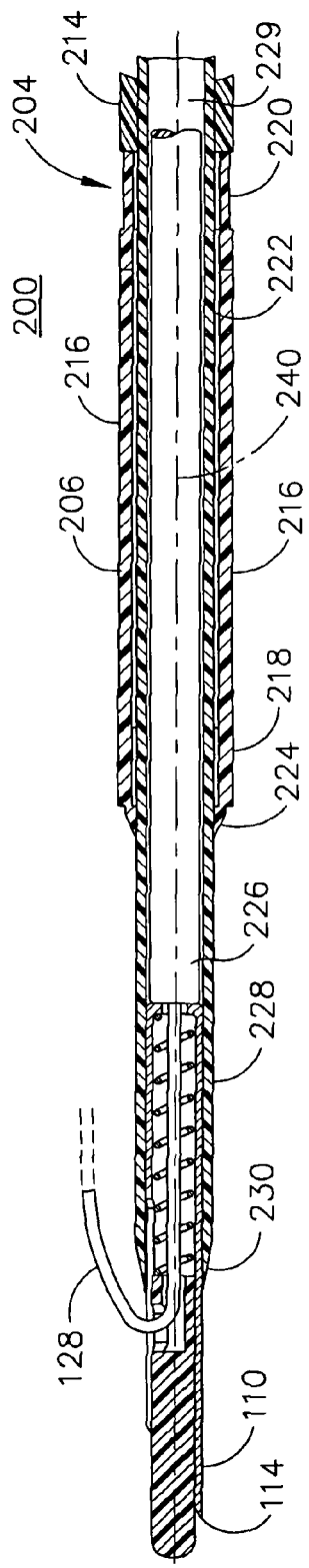
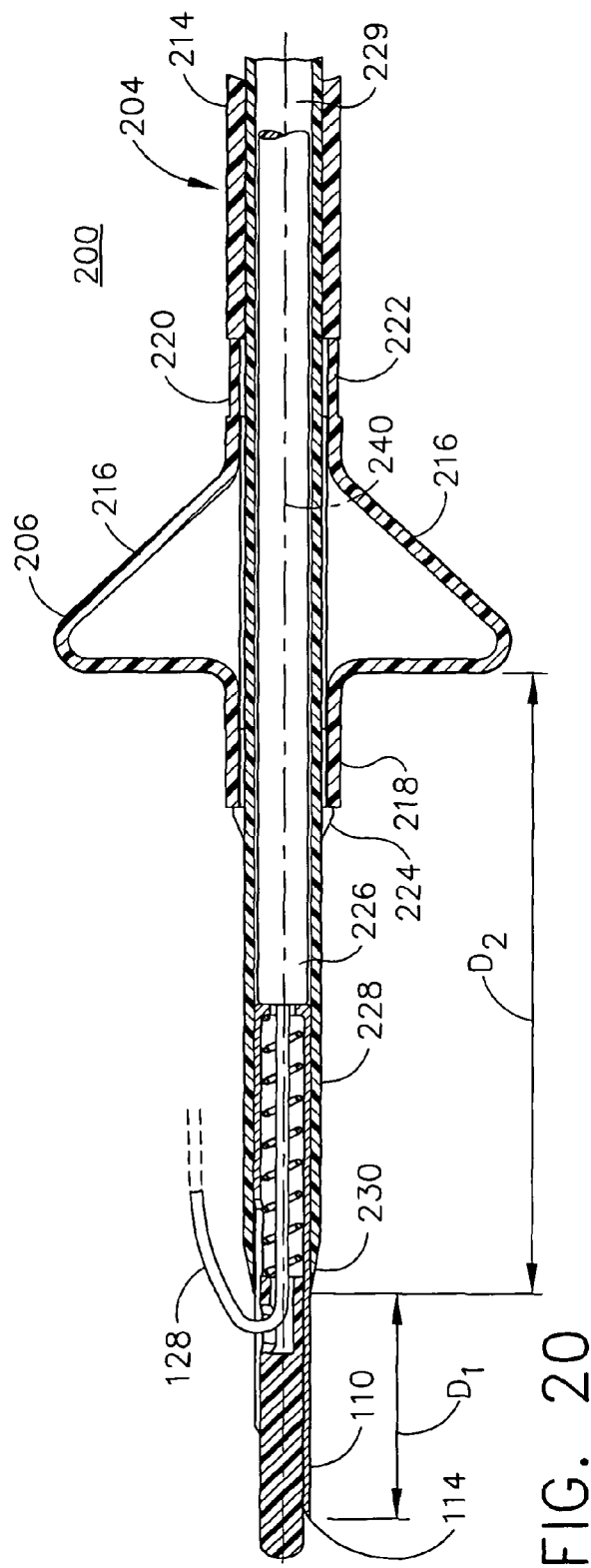

SELF-SHIELDING SUTURE ANCHOR

BACKGROUND

The present application relates to surgical fasteners and instruments for approximating and fastening tissue and, more particularly, to suture anchors and associated instruments for endoscopically attaching sutures to tissue.

The working channel of a flexible endoscope typically has a diameter in the range of about 2.5 to about 4 millimeters. Current staplers and suturing devices cannot be easily redesigned to work through such small openings. In addition, performing procedures by way of the working channel does not easily permit using two instruments positioned at different angles with respect to the wound site in order to "pass and catch" a needle and apply sutures.

Various clips, suture fasteners and anchors have been developed such that physicians (e.g., gastroenterologists) may endoscopically close perforations in the gastrointestinal tract resulting from, for example, ulcers or polypectomy. One type of suture anchor is known as a "T-tag" fastener. The T-tag is a small metallic pin with a suture attached at the middle. The physician may load the T-tag into the end of a cannulated needle of an applicator that may be inserted through the working channel of a flexible endoscope. The physician may push the needle into the tissue near the perforation and implant the T-tag into the tissue with the attached suture trailing through the working channel and out the proximal end of the endoscope. After two or more T-tags are attached to the tissue near the wound in this manner, the physician may pull the sutures to oppose the tissue around the wound. The physician may then fasten the sutures together by applying a plurality of alternating, right and left overhand knots using a knot pushing device or by applying a knotting element or other type of fastener through the working channel of the endoscope.

In order for T-tags to resist pull-out from the tissue when the attached suture is tensioned, the T-tag should rotate after ejection from the cannulated needle to be approximately perpendicular to the attached suture. An issue typically associated with anchors such as the T-tag is that if the anchor is implanted within tissue layers, rather than through tissue layers such that the anchor cannot reorient as described, it is possible for the T-tag to be easily pulled from the hole created by the penetrating needle.

Another issue typically associated with current suture anchors such as the T-tag is the occasional situation in which the anchor comes out of the distal end of the cannulated needle while the applicator is manipulated into the endoscope and towards the wound site.

An issue typically associated with current suture anchor applicators is the risk that nearby organs may be accidentally injured by the needle of the applicator. The physician normally cannot see anatomical structures on the distal side of the tissue layers when the needle is being pushed through the tissue layers. Therefore, there is a risk that adjacent organs may be accidentally injured by the penetrating needle.

In addition to addressing the above issues, it may be desirable to provide an improved suture anchor that is magnetic resonance imaging (MRI) compatible. For example, the anchor may be formed from a non-ferrous material.

Accordingly, there is a need for an improved suture anchor that may be securely retained in a suture anchor applicator until deployment into the tissue near a wound. In addition, there is a need for a suture anchor with improved resistance to pull-out from tissue, whether implanted within tissue layers or through tissue layers. Furthermore, there is a need for an improved suture anchor and suture anchor applicator that helps to prevent accidental injury to nearby anatomical structures during deployment of the anchor into tissue near a wound site. Finally, there is a need for an improved suture anchor that may be formed from a non-ferrous material in order to be MRI compatible.

SUMMARY

In one embodiment, a self-shielding suture anchor is provided and includes a body having a proximal end and a distal end, the distal end including a penetrating tip. The suture anchor also includes a shielding element movable relative to the distal end between a shielding position, wherein the shielding element is distal to the penetrating tip, and a retracted position, wherein the shielding element is proximal to the penetrating tip. The suture anchor also includes a spring element operatively associated with the shielding element to bias the shielding element to the shielding position.

In another embodiment, a self-shielding suture anchor is provided and includes a body having a proximal end and a distal end, the distal end including a penetrating tip. The body is formed from a metallic tube and the penetrating tip is formed by grinding the distal end. The suture anchor further includes a shielding element slidably retained inside of the body and movable relative to the distal end between a shielding position and a retracted position, wherein the shielding element has a blunt end distal to the penetrating tip in the shielding position and proximal to the penetrating tip in the retracted position. The suture anchor further includes a spring element slidably retained inside of the body and operatively connected to the shielding element to bias the shielding element to the shielding position, wherein the spring element is a metallic coil spring.

Other aspects and embodiments of the self-shielding suture anchor will become apparent from the following description, the accompanying drawings and the appended claims.

BRIEF DESCRIPTION OF THE DRAWINGS

FIG. 6 is a longitudinal sectional view of the distal portion of a first embodiment of a suture anchor applicator, shown while a suture anchor is in a loaded position;

FIG. 7 is a longitudinal sectional view of the applicator shown in FIG. 6, shown after the suture anchor has been deployed;

FIG. 19 is a longitudinal sectional view of the distal end of the applicator shown in FIG. 18, showing the suture anchor of FIG. 16 in a loaded position and the tissue stop in a collapsed configuration;

FIG. 20 is a longitudinal sectional view of the distal end of the applicator shown in FIG. 18, showing the suture anchor of FIG. 16 in a loaded position and the tissue stop in an expanded configuration;

FIGS. 23, 24, 25, 26, 27 and 28 illustrate a method of attaching a suture anchor to the tissue of a patient, showing the distal portion of the applicator and the suture anchor of FIG. 21, wherein FIG. 23 shows positioning the distal end of the applicator containing the suture anchor near the tissue, FIG. 24 shows pushing the suture anchor against the tissue, FIG. 25 shows piercing the needle tip of the suture anchor into the tissue, FIG. 26 shows penetrating the suture anchor and the distal end of the applicator through the tissue to a predetermined maximal penetration depth, FIG. 27 shows deploying the suture anchor, and FIG. 28 shows withdrawing the applicator from the tissue such that the suture anchor is attached to the tissue.

DETAILED DESCRIPTION

Figure 1:
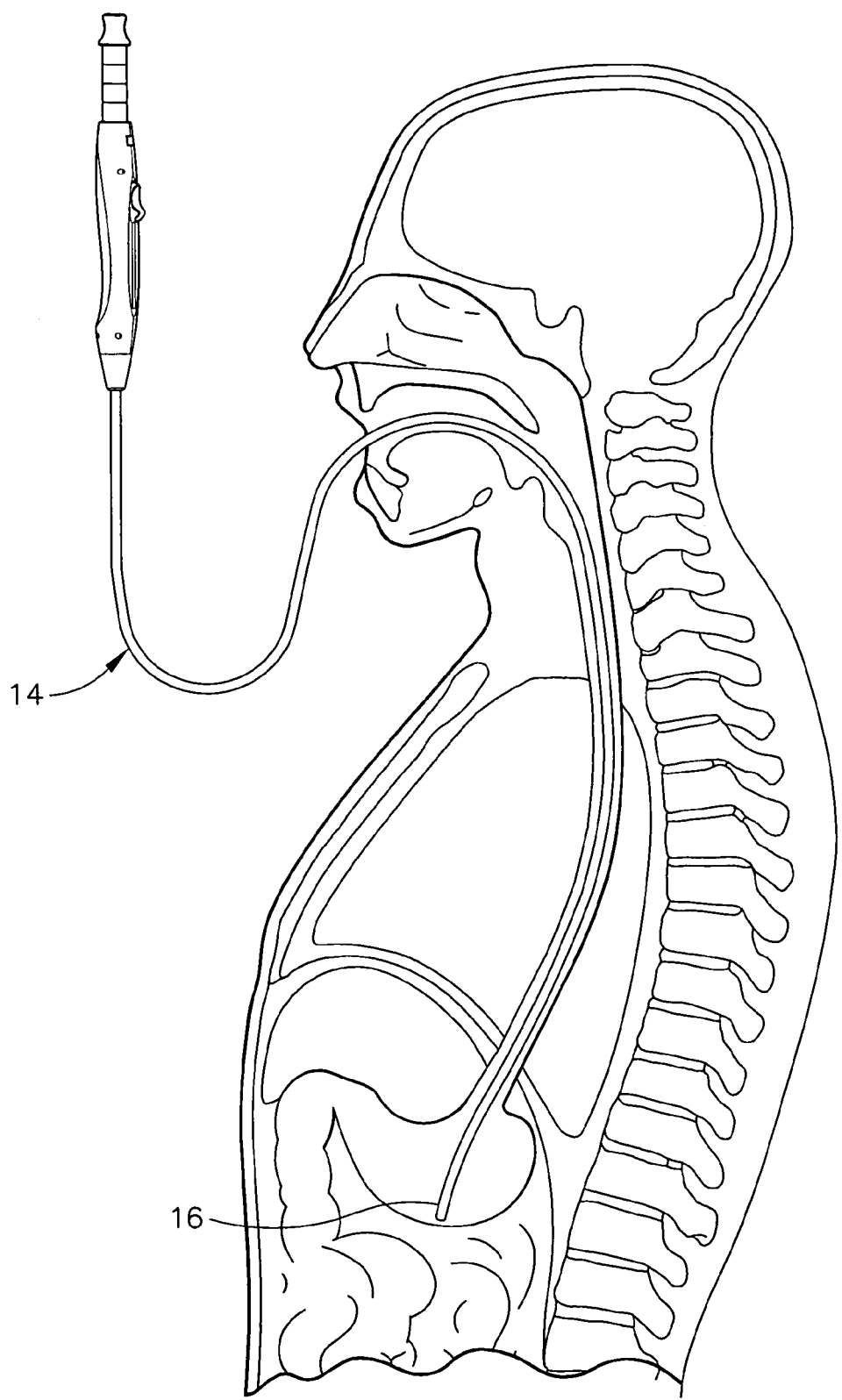
FIG. 1 is a drawing of a flexible, endoscopic portion of a gastroscope inserted into the upper gastrointestinal tract of a patient.
Figure 2:
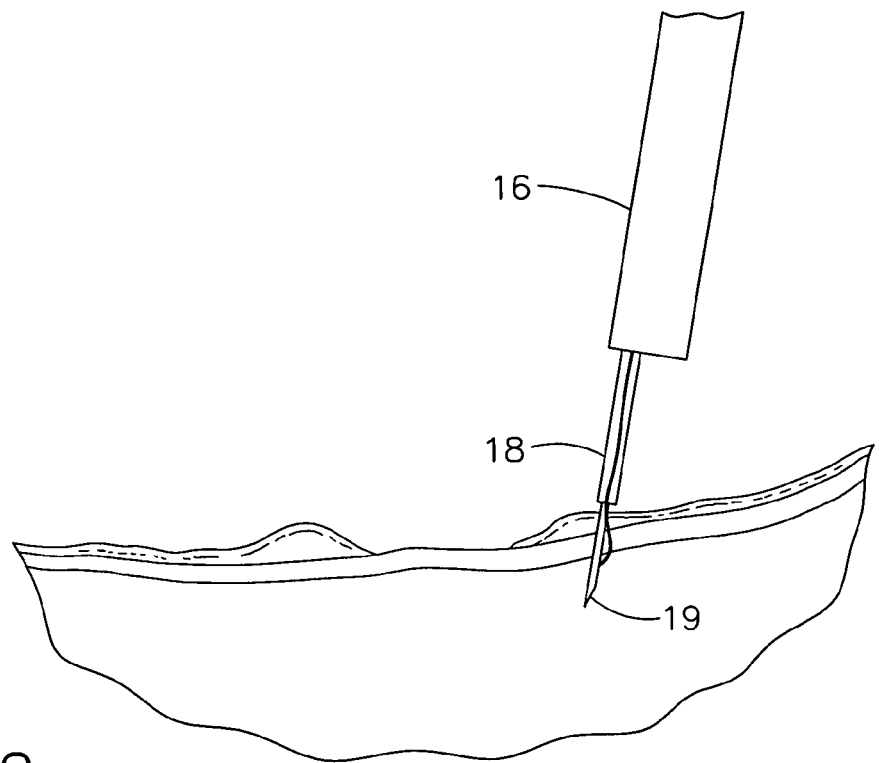
FIG. 2 is a drawing of the distal portion of a suture anchor applicator extending from the distal end of the gastroscope while a first suture anchor is deployed into the stomach wall near a wound.
Figure 3:
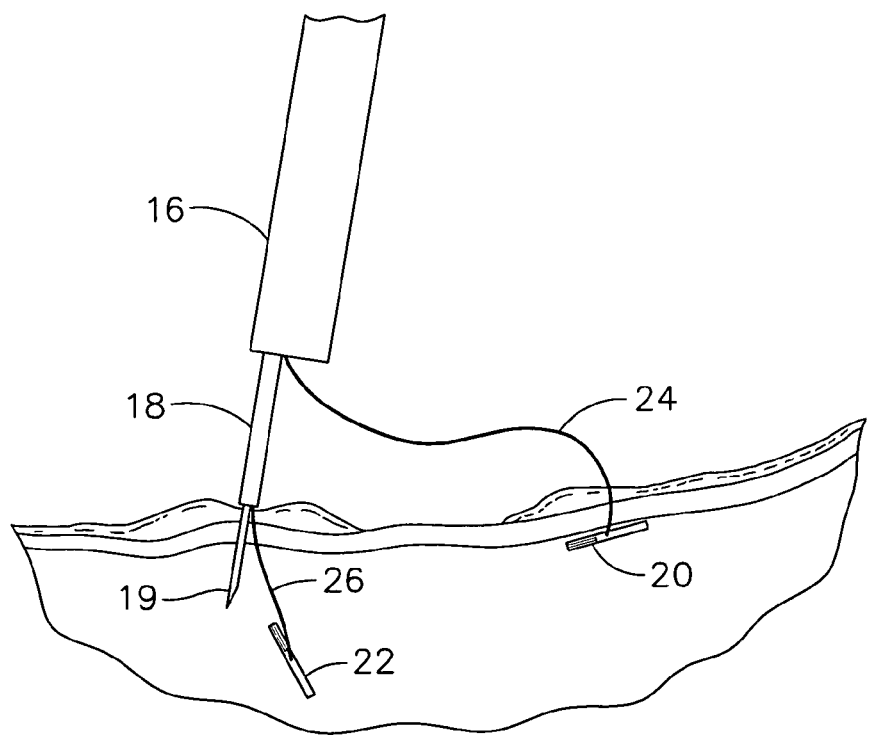
FIG. 3 is a drawing of the applicator of FIG. 2 while a second suture anchor is deployed into the stomach wall on the opposing side of the wound.
Figure 4:
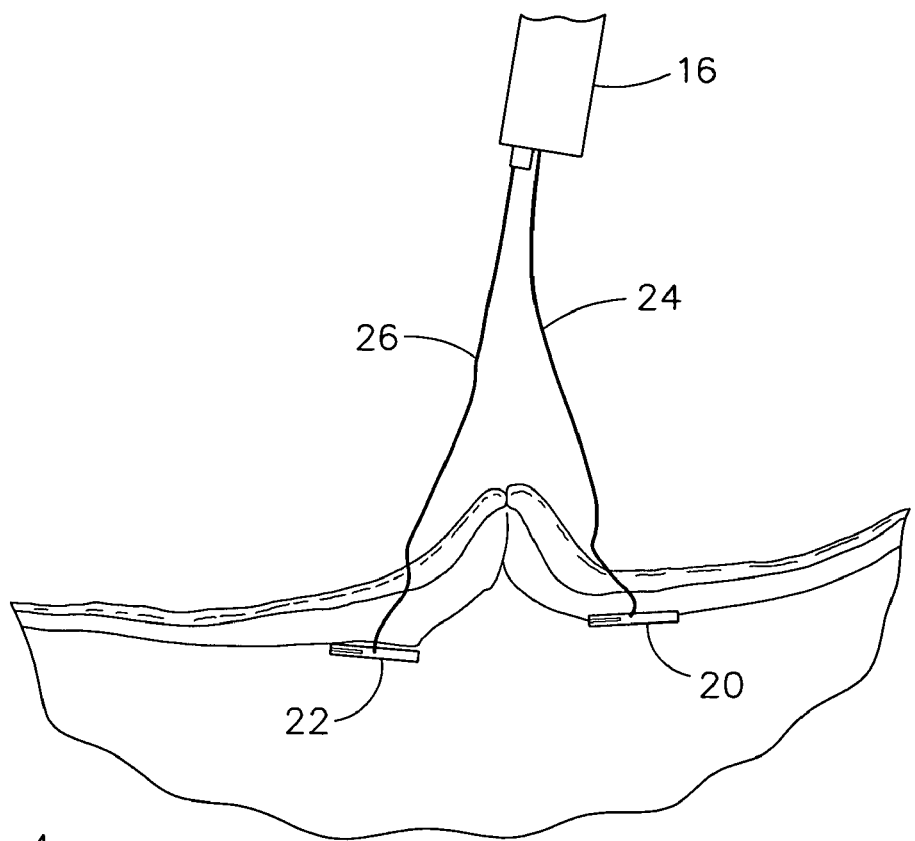
FIG. 4 is a drawing of the applicator of FIG. 2 while a pair of sutures of the first and second suture anchors are drawn together to oppose the tissue on each side of the wound.
Figure 5:
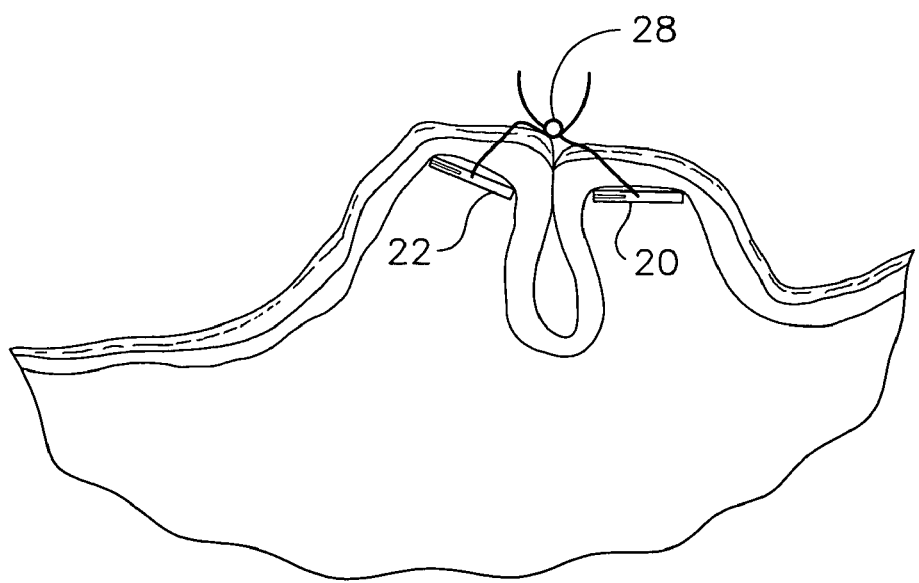
FIG. 5 is a drawing of the pair of sutures of FIG. 4 fastened together with a knotting element, thereby holding the tissue in apposition.

FIG. 1 illustrates a flexible endoscopic portion 16 of a gastroscope 14 inserted into the upper gastrointestinal tract of a patient. FIGS. 2, 3, 4 and 5 illustrate a procedure for repairing a wound such as a gastric bleeding ulcer in the stomach wall of the patient via the working channel of gastroscope 14. As shown in FIG. 2, the physician (e.g., gastroenterologist) inserts a suture anchor applicator 18 through gastroscope 14 and penetrates a cannulated needle 19 through the stomach wall near the diseased area or wound. Needle 19 contains at least one suture anchor such that, as shown in FIG. 3, the physician may deploy a first suture anchor 20 attached to a first suture 24 to one side of the wound and a second suture anchor 22 attached to a second suture 26 to the opposite side of the wound. First and second suture anchors 20, 22 may be conventional "T-tag" fasteners or any of the suture anchor embodiments described herein or their equivalents. The free ends of first and second sutures 24, 26 may extend through the proximal end of gastroscope 14 such that, as shown in FIG. 4, the physician may draw the first and second sutures 24, 26 together to oppose the tissue around the wound. The physician may then fasten the first and second sutures 24, 26 together by, for example, applying a plurality of alternating, right and left overhand knots using a knot pushing device (not shown) or by applying a knotting element 28 or other type of fastener, as shown in FIG. 5, by way of the working channel of gastroscope 14. Excess suture may be trimmed near the knot using an endoscopic cutting instrument.

When using conventional T-tag fasteners with the technique shown in FIGS. 2-5, there are necessary conditions for the T-tag fasteners to become securely attached to the tissue. For example, it is important that the T-tag fastener reorient with respect to the suture as previously described such that the T-tag may not be easily pulled through the tissue. If the T-tag is positioned within the tissue rather than completely through the tissue into a body cavity, the T-tag still must reorient to some degree such that the suture is securely attached to the tissue.

Although the size of the cannulated needle 19 shown in FIG. 2 may vary, it may have an inner diameter of less than one millimeter. Consequently, suture anchor 22 must be very small to be loaded inside of needle 19, yet once deployed into tissue, must be sufficiently broad to resist pull-out from tissue such that considerable tension may be applied to the sutures to draw together the tissue. Therefore, it would be desirable for suture anchor 22 to expand once deployed from the applicator and/or to include features to help secure anchor 22 to the tissue. In addition, it would be desirable for suture anchor 22 to remain securely in the loaded position within applicator 18 prior to deployment into tissue to avoid the time-consuming steps of withdrawing, reloading and reinserting the applicator.

Recently, a number of medical devices have been developed that provide an auxiliary passageway along the outside of the endoscope. One example of a medical apparatus that provides an auxiliary endoscopic passageway may be found in U.S. patent application Ser. No. 10/440,957 (published as U.S. Patent Pub. No. 2004/0230095), filed May 12, 2003, and assigned to Ethicon Endo-Surgery, Inc. The auxiliary passageway may be used, perhaps in combination with the working channel of the endoscope, for several purposes, such as to insert a suture anchor applicator for access to an internal wound site. It should be understood, therefore, that descriptions herein referring to the working channel of the endoscope also include using such an auxiliary passageway.

FIGS. 6 and 7 are longitudinal sectional views of the distal portion of a first embodiment of a suture anchor applicator 30, which may be used in the same manner as described for applicator 18 of FIGS. 2 and 3. In FIG. 6, a first aspect of a suture anchor 52 is shown in a loaded position in applicator 30. In FIG. 7, suture anchor 52 is shown deployed from applicator 30. Applicator 30 may have a shaft 31 that includes an inner tube 40 and an outer tube 42. In a first aspect of applicator 30, shaft 31 may be adapted for insertion into the working channel of a flexible endoscope, including a gastroscope and a colonoscope, by being flexible and having an outer diameter approximately in the range of 2 to 3.8 millimeters and a length of approximately one and a half meters. In a second aspect of applicator 30, shaft 31 may be adapted for percutaneous or laparoscopic applications and be relatively rigid and straight, and may have a length approximately in the range of 20-200 centimeters.

Outer tube 42 may be formed from an extruded polymer, a helically wound metallic wire or from other materials well-known in the art. Inner tube 40 may be formed from 19 gage stainless steel hypodermic tubing, for example, having an outer diameter of approximately 0.043 inches (1.09 millimeters) and a wall thickness of approximately 0.003 inches (0.076 millimeters). The distal end of inner tube 40 may be ground to form a cannulated needle 32 having a distal, penetrating tip 34. Alternatively, inner tube 40 may be formed from an alternate type of metallic or polymeric tube and attached to cannulated needle 32, such as by welding, crimping, gluing or other conventional method.

Penetrating tip 34 may be ground to have a "bi-angular" configuration as shown in FIG. 6. To facilitate placement of the suture anchor into the body, the outer surface of needle 32 may be textured, coated or otherwise processed to enhance the ultrasonic reflectivity of needle 32 such that the physician may view needle 32 from outside of the patient's body using, for example, a handheld ultrasonic imaging device.

Inner tube 40 and needle 32 may include a channel 36 extending along a longitudinal axis 50 between the proximal and distal ends of applicator 30. At least one suture anchor 52 having a suture 48 attached thereto may be loaded in channel 36. An actuating element 38 may extend through channel 36 of applicator 30 for ejecting suture anchor 52 out of needle 32, as shown in FIG. 7.

Outer tube 31 may be moved between an extended position for shielding tip 34 of needle 32 (FIG. 6) and a retracted position for exposing tip 34 of needle 32 (FIG. 7). Shaft 31 may be inserted into the working channel or auxiliary passageway of the endoscope with suture 48 trailing in the diametral clearance between shaft 31 and the inside of the working channel or passageway, such that the free end of suture 48 may extend out of the proximal end of the channel or passageway.

Expandable Suture Anchor

Numerous aspects of an expandable suture anchor are described herein. In general, the expandable suture anchor may be used for attaching a suture to any one of numerous soft tissues, including the wall of the gastrointestinal tract. The anchor may include a suture attached thereto and a body that is constrainable to a first configuration for deployment into the tissue and that is expandable when unconstrained to a second configuration for resisting pull-out from the tissue.

Figure 8:
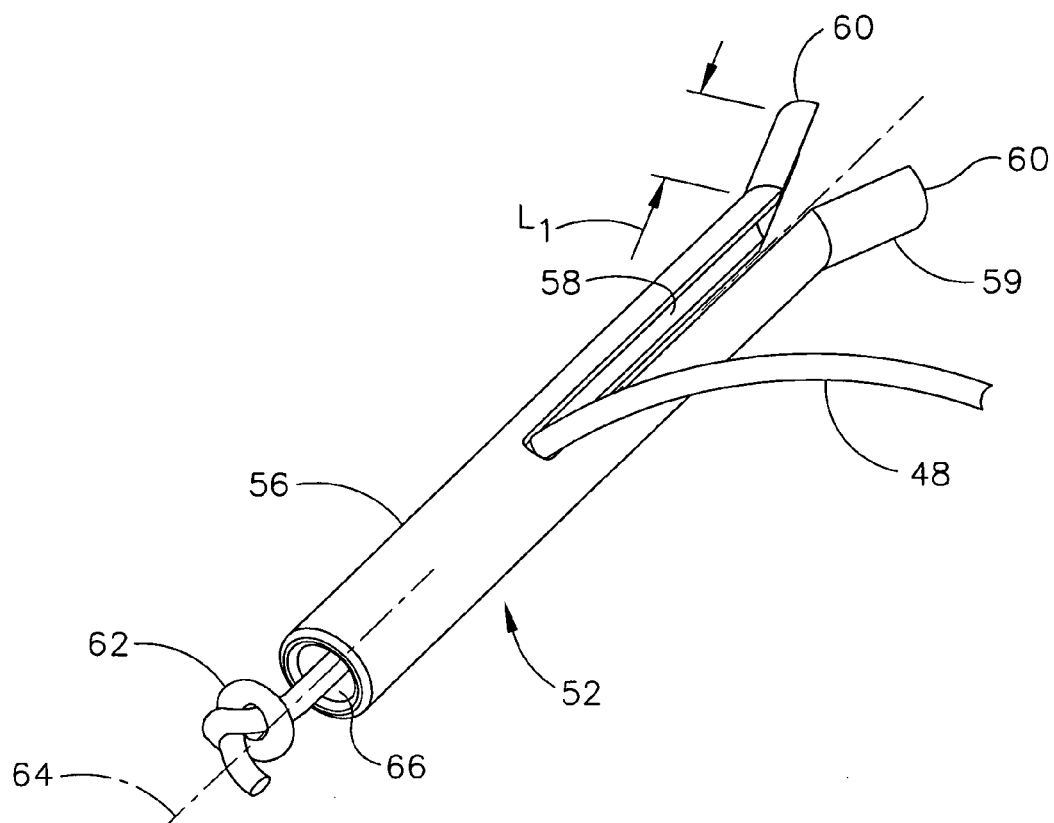
FIG. 8 is a perspective view of a first aspect of a suture anchor while in an unconstrained configuration.
Figure 9:
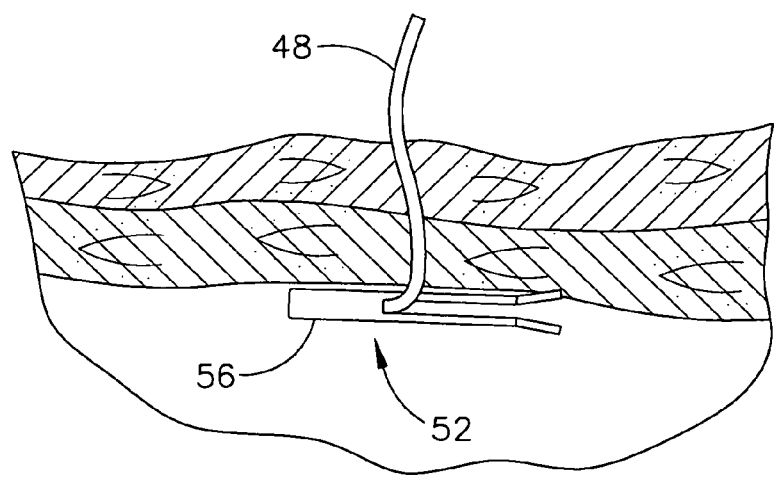
FIG. 9 is a drawing of the suture anchor of FIG. 8 after placement through the tissue layers.

FIG. 8 is a perspective view of the first aspect of the suture anchor 52 shown with applicator 30 in FIG. 6. FIG. 9 shows anchor 52 after placement through tissue layers such as the stomach wall. Anchor 52 may include a body 56 having a bifurcated portion 58 along an anchor axis 64 and forming a pair of legs 60. Bifurcated portion 58 may include an angled portion 59 that splays away from axis 64. Angled portion 59 has a length indicated by "L1" that may vary, for example, between approximately one eighth and one quarter of the overall length of anchor 52. Anchor 52 may have a first configuration when constrained in the loaded position in needle 32 (see FIG. 6) and a second configuration when unconstrained as shown in FIG. 8. Anchor 52 may have a relatively short, angled portion 59 as depicted in FIG. 8 to help retain anchor 52 securely inside of needle 32 until deployment of anchor 52 into tissue. Anchor 52 may be positioned inside of channel 36 of needle 32 such that legs 60 bear against the inside of channel 36, causing body 56 to bow as shown in FIG. 6.

Anchor 52 may be formed from a biocompatible, spring material such as a stainless steel, a titanium alloy, a nickel-titanium memory metal (Nitinol), a polymer, or an absorbable polymer. Spring material shall be referred to herein as a material such that, a suture anchor formed from the spring material is biased to springably change from the first to the second configuration when not constrained.

Suture 48 and all the sutures described herein may be a surgical suture formed from convention surgical suture materials including, for example, cat gut, polypropylene, polyester and stainless steel. The suture size may be any one of the commonly used sizes for surgical procedures, including 2/0, 3/0 and 4/0 sutures.

As shown in FIG. 8, anchor 52 may include a bore 66. A suture 48 may be attached to anchor 52 by passing suture 48 through bore 66 and tying a knot 62 that is larger than bore 66. Alternately, a ferrule 47 (see FIG. 7) may be crimped onto suture 48. It is also possible to crimp or stake body 56 onto suture 48 at the end opposite of legs 60. Suture 48 may also be glued or mechanically attached to anchor 52, or by any one of numerous other conventional methods.

Suture 48 may extend from the middle portion of anchor 52 such that when suture 48 is drawn tightly after placement of anchor 52 through layers of tissue, anchor 52 reorients such that axis 64 is approximately perpendicular to suture 48 extending from the wound site, thereby providing a high resistance to pull-out from the tissue. If anchor 52 is positioned within tissue rather than in a body cavity, legs 60 also function to dig into the tissue when a tensile force is applied to suture 48, thereby helping anchor 52 reorient within the tissue such that suture 48 is securely attached to the tissue. The lengths L1 of legs 60 and the angles formed by legs 60 relative to axis 64 may be selected such that tissue retention forces are asymmetric when a tensile force is applied to suture 48, thereby helping anchor 52 to reorient within the tissue and increase the pull-out resistance.

In one aspect, the diameter of anchor 52 may be approximately 0.50 to 0.85 millimeters, or small enough to slide easily, for example, into a 19 gage, cannulated needle. The overall length of anchor 52 may be, but is not limited to, approximately five to 10 millimeters.

Figure 10:
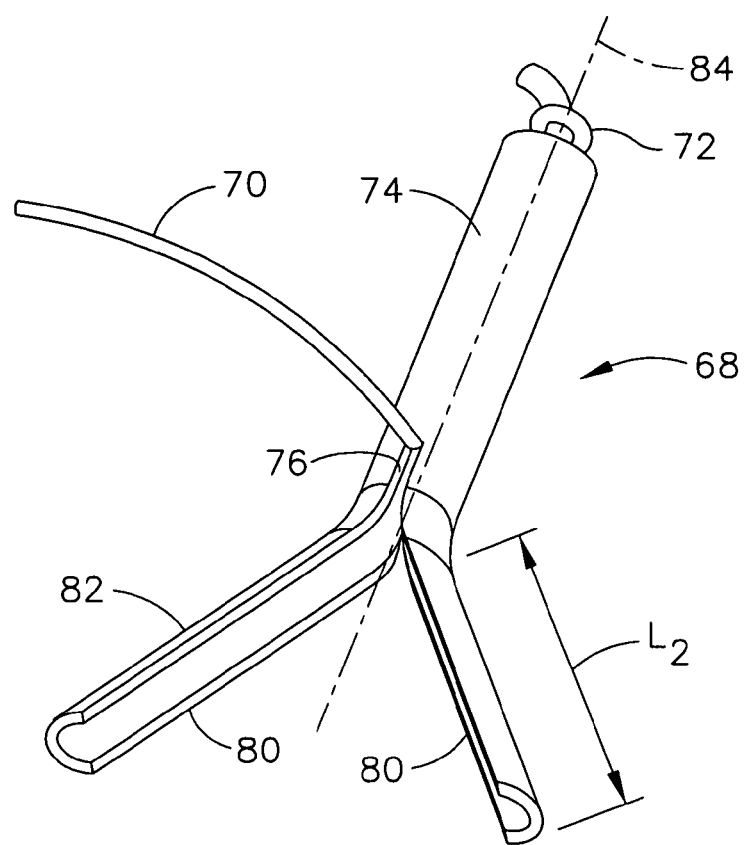
FIG. 10 is a perspective view of a second aspect of a suture anchor while in an unconstrained configuration.
Figure 11:
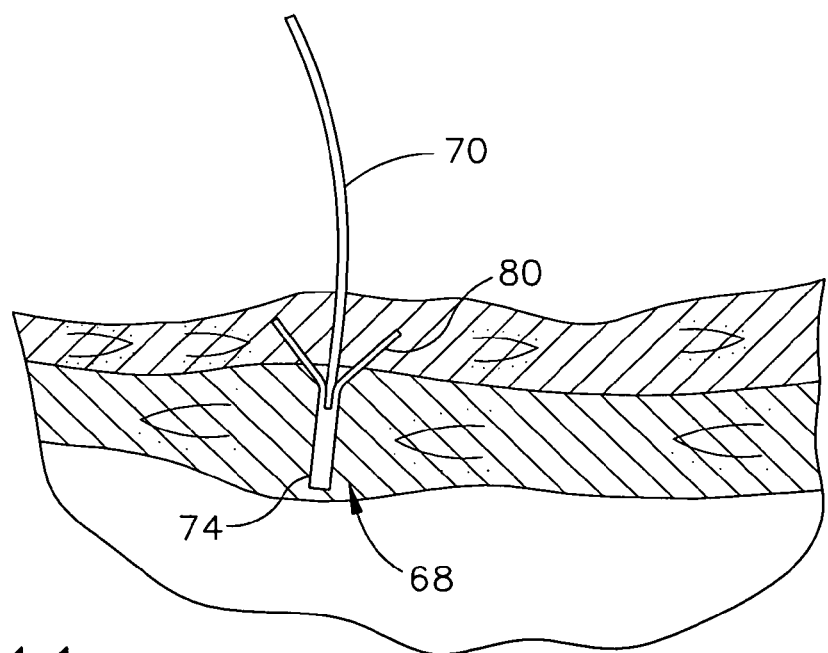
FIG. 11 is a drawing of the suture anchor of FIG. 10 after placement within the tissue layers.

FIG. 10 is a perspective view of a second aspect of a suture anchor 68. FIG. 11 shows anchor 68 after placement in the tissue layers. Anchor 68 has a first configuration when constrained in the loaded position inside of needle 32 of applicator 30 (FIG. 6) and a second configuration when unconstrained, as shown in FIGS. 10 and 11. The second configuration is broader in at least one plane than the first configuration. Anchor 68 may have at least one leg 80 splayed at an angle or extending outwardly relative to a longitudinal axis 84. As shown in FIG. 10, anchor 68 may include a body 74 having a bifurcated portion 76 forming a pair of legs 80. Anchor 68 may also have a plurality of legs. For example, anchor 68 may have a large plurality of very slender legs formed from stiff filaments and joined together in a "broom-like" fashion. In the latter situation, the plurality of legs may provide a scaffold for tissue ingrowth, which is beneficial for further securing anchor 68 to the tissue.

Anchor 68 is similar to anchor 52 of FIG. 8, except that an angled portion 82 of anchor 68 is longer, as indicated by "L2", than angled portion 59 of anchor 52. Length L2 may be, for example, approximately one quarter to one half of the overall length of anchor 68. Anchor 68 may be formed from the same biocompatible, spring materials as described for anchor 52. A suture 70 may be attached to anchor 68 by a knot 72, a crimped ferrule, glue or any one of numerous other conventional methods.

Anchor 68 provides a high pull-out resistance from tissue when deployed either through tissue layers or within tissue layers. In the former, anchor 68 may orient itself to be approximately perpendicular to suture 70. In the latter, legs 80 of anchor 68 act like barbs and may dig into surrounding tissue. In addition, the spring-back of legs 80 helps to hold anchor 68 securely inside of needle 32 of applicator 30 (FIG. 6).

Figure 12:
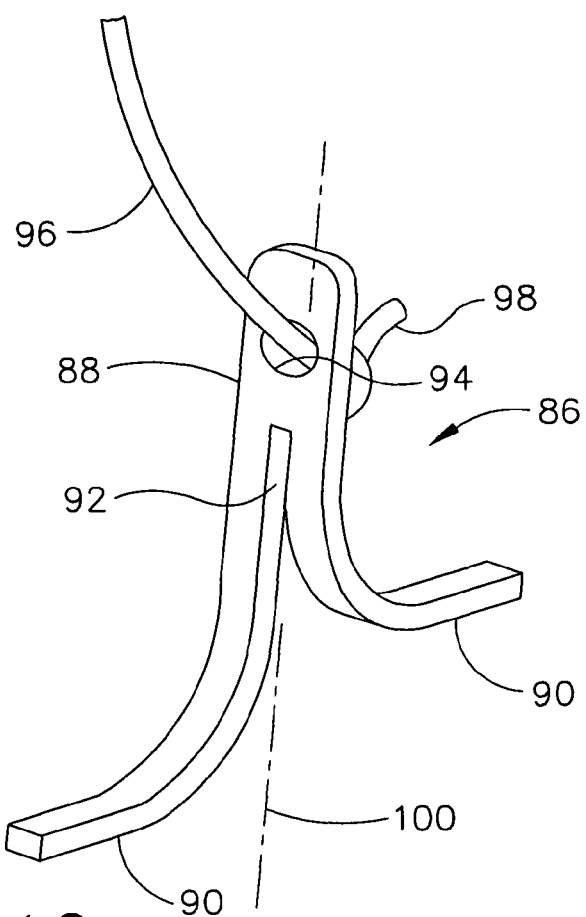
FIG. 12 is a perspective view of a third aspect of a suture anchor while in an unconstrained configuration.
Figure 13:
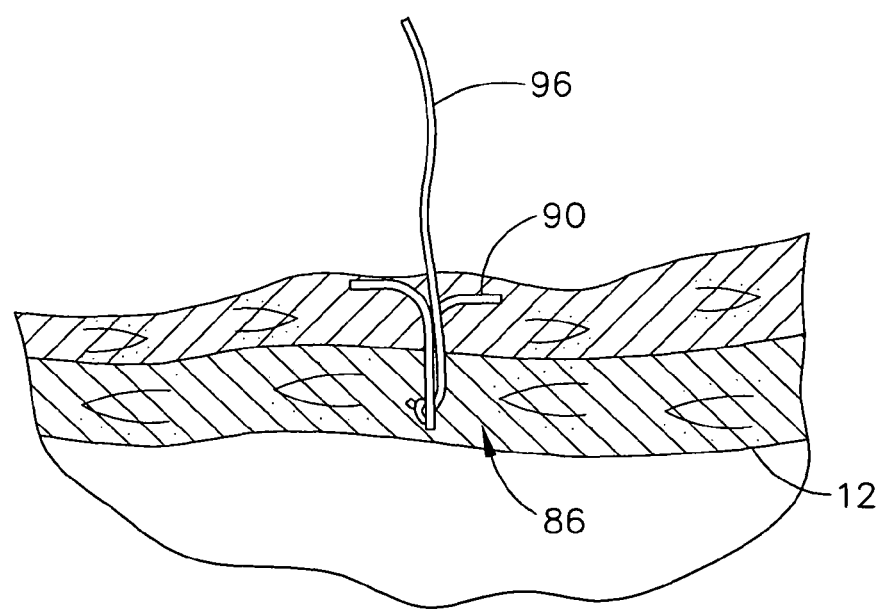
FIG. 13 is a drawing of the suture anchor of FIG. 12 after placement within the tissue layers.

FIG. 12 shows a third aspect of a suture anchor 86 in an unconstrained, second configuration. FIG. 13 shows anchor 86 also in the second configuration, after placement within stomach wall 12. Anchor 86 has a constrained, first configuration when in the loaded position in needle 32 of applicator 30 (FIG. 6). Anchor 86 is a new adaptation of a surgical clip concept disclosed in U.S. Pat. No. 6,447,524, which is titled "Fastener for Hernia Mesh Fixation," issued to Knodel et al. on Sep. 10, 2002 and assigned to Ethicon Endo-Surgery, Inc. Anchor 86 may be formed from a titanium-nickel memory metal (Nitinol), a stainless steel, a titanium alloy, or any one of a number of spring materials. Anchor 86 may include a body 88 having a bifurcation 92 to form a pair of legs 90 that splay or extend outwardly from an anchor axis 100. A suture 96 may be retained in a hole 94 in body 88 by a knot 98. When in the loaded position inside of needle 32 of applicator 30 (FIG. 6), legs 90 may extend in the distal direction. Like anchor 68 of FIG. 10, anchor 86 may provide a high pull-out resistance from tissue when placed both through and within tissue layers.

Figure 14:
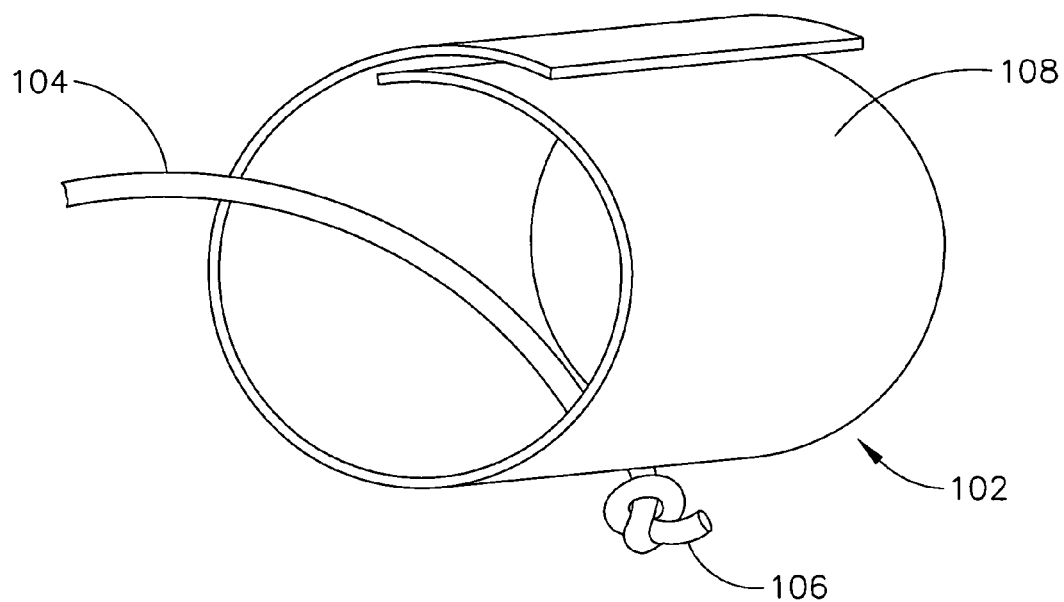
FIG. 14 is a perspective view of a fourth aspect of a suture anchor while in a constrained configuration.
Figure 15:
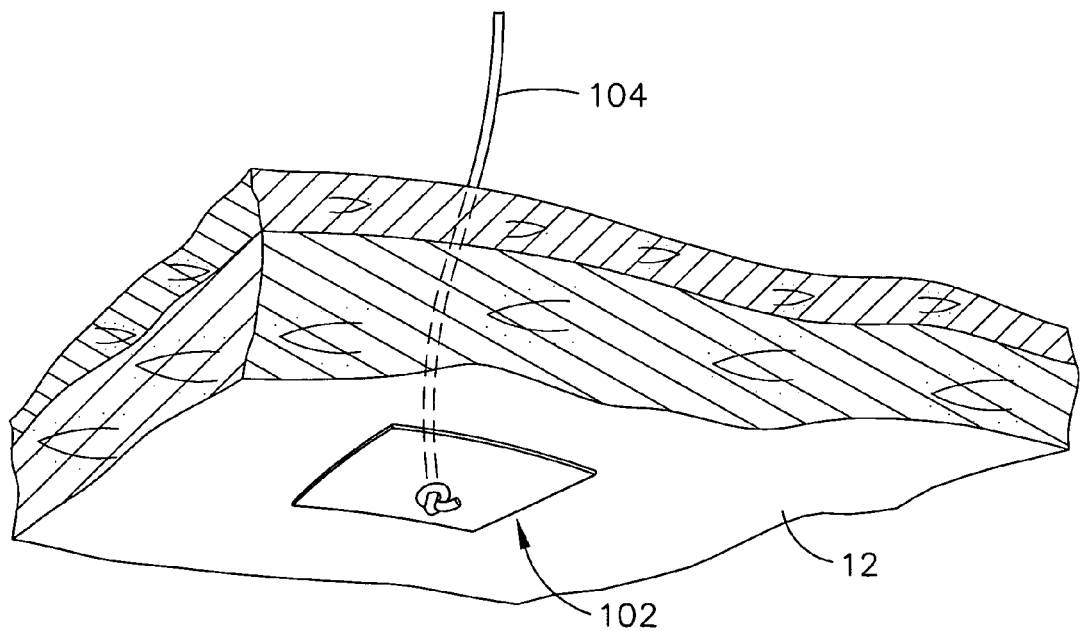
FIG. 15 is a drawing of the suture anchor of FIG. 14 after placement through the tissue layers.

FIG. 14 illustrates a fourth aspect of a suture anchor 102 while in a first configuration, such as when constrained in a loaded position in needle 32 of applicator 30 (FIG. 6). FIG. 15 shows anchor 102 placed through stomach wall 12, unconstrained and in a second configuration. Anchor 102 has a body 108 that may be formed from a spring material such as stainless steel, titanium alloy, a polymer or a memory metal (Nitinol) into a thin sheet, flat or plate that may be rolled into the approximately cylindrical shape of the first configuration. When unconstrained in the second configuration, anchor 102 may have a relatively large planar surface area as compared to the projected area of anchor 102 while in the first configuration, thereby providing a very high pull-out resistance from tissue when placed through tissue layers as shown in FIG. 15. Body 108 may have a rectangular shape with side dimensions of approximately 5 to 10 millimeters, although body 108 may have any one of many other geometric shapes. Body 108 may be sufficiently thick to attach securely to suture 104 and to resist excessive deformation during normal tensioning of suture 104. Body 108 may be formed from a sheet of Nitinol, for example, that has a thickness of about 0.05 to 0.2 millimeters.

Anchor 102 may include a suture 104 retained through a hole (hidden) by a knot 106. Alternately, suture 104 may be attached to anchor 102 by gluing, crimping or any one of a number of well known methods.

Self-Shielding Suture Anchor

As already described, a physician may fully penetrate the needle of a suture anchor applicator through tissue layers of an organ in order to deploy the suture anchor on the distal side of the tissue layers. The physician normally cannot see anatomical structures on the distal side of the tissue layers through the endoscope and therefore may accidentally injure nearby organs with the penetrating needle. A fifth aspect of a suture anchor 110, a "self-shielding" suture anchor, is provided to help prevent such accidental injury.

Figure 16:
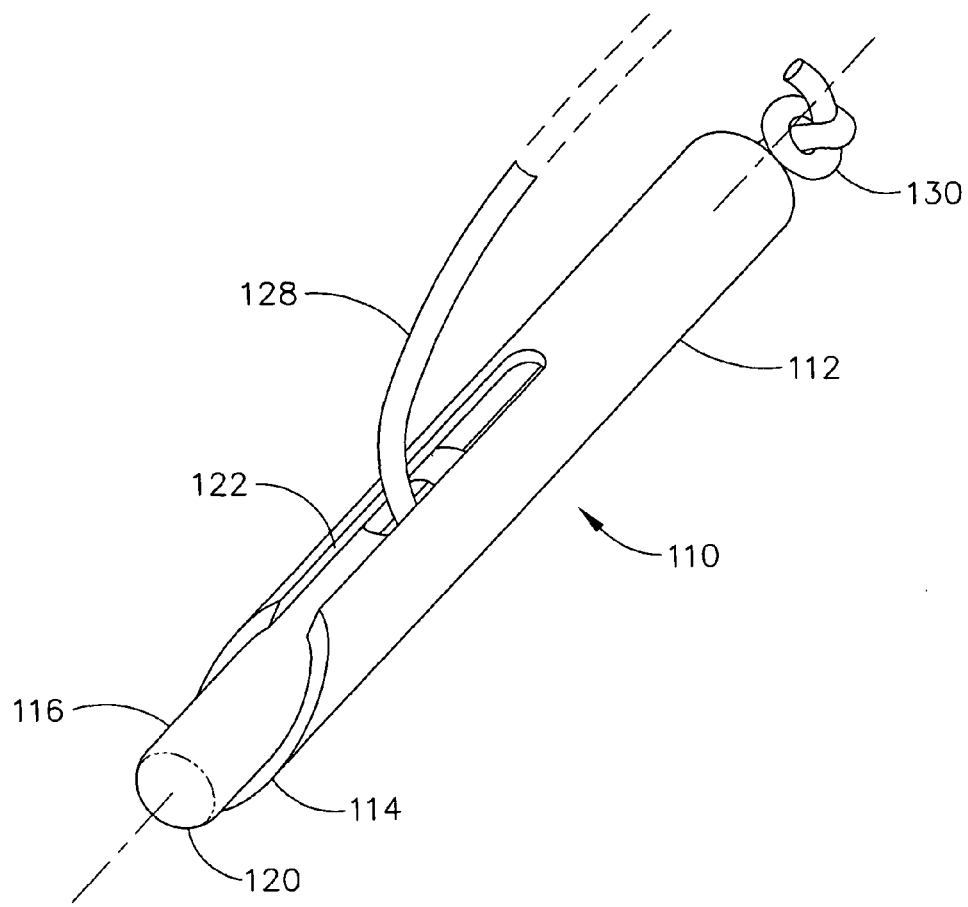
FIG. 16 is an perspective view of a fifth aspect of a suture anchor while in an unconstrained configuration.
Figure 17:
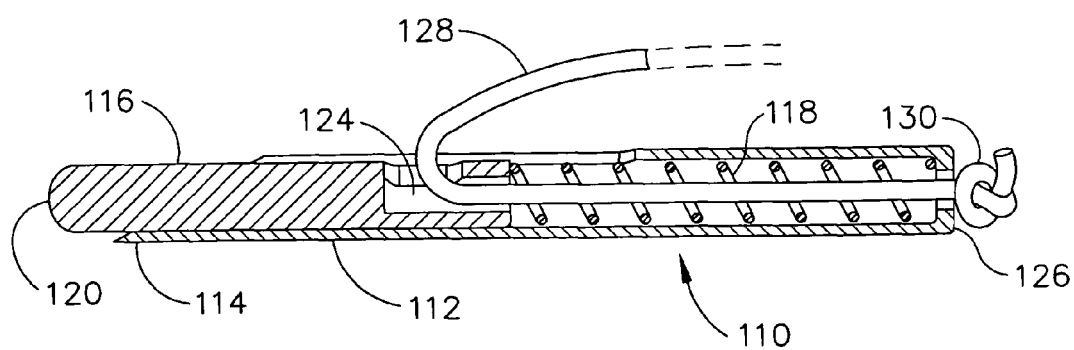
FIG. 17 is a longitudinal sectional view of the suture anchor of FIG. 16.

FIG. 16 is a perspective view and FIG. 17 is a longitudinal sectional view of anchor 110, which includes a body 112 having a penetrating tip 114, a shielding element 116 and a spring element 118. Shielding element 116 may be retained in body 112 and may have a blunt end 120 that is movable between a shielding position that is distal to penetrating tip 114 and a retracted position that is proximal to penetrating tip 114. FIGS. 16 and 17 show shielding element 116 in the shielding position. Spring element 118 (FIG. 17) may be operatively associated with penetrating element 114 and shielding element 116, such that spring element 118 may apply a predetermined spring force to bias shielding element 116 to the shielding position. Shielding element 116 can move to the retracted position when blunt end 120 is pushed against tissue with a force greater than the spring force, such that penetrating tip 114 can penetrate tissue. Once penetrating tip 114 has penetrated through the tissue, blunt end 120 can immediately extend to the shielding position to help prevent accidental injury to nearby anatomical structures.

Still referring to FIGS. 16 and 17, body 112 may be formed into a tubular shape from a stainless steel, titanium alloy, or other biocompatible metal. The outside diameter of body 112 may be approximately in the range of 0.5 to 0.85 millimeters and the length may be approximately in the range of 10 to 15 millimeters. Spring element 118 may be a metallic coil compression spring that inserts easily into body 112 or spring element 118 may be formed from any one of numerous other biocompatible materials that can provide a spring force to bias shielding element 116 to be in the shielding position. Shielding element 116 may have a cylindrical, bullet shape that slides easily in body 112 and may be formed from a biocompatible metal or polymer. Body 112 of anchor 110 may include a slot 122 extending longitudinally from penetrating tip 114 to approximately halfway between tip 114 and a trailing end 126 of body 112. A suture 128 may pass through slot 122, a passage 124 of shielding element 116 and the coils of spring element 118, and may be attached to trailing end 126 by a knot 130 or by any one of numerous other suitable methods including gluing, crimping and staking. This attachment method of suture 128 also may function to retain shielding element 116 and spring element 118 inside of body 112.

Since anchor 110 includes a penetrating tip 114, it is not necessary for the applicator of anchor 110 to also include a needle with a penetrating tip. For example, needle 32 of applicator 30 in FIG. 6 may be replaced with a short tube attached to inner tube 40, or inner tube 40 may merely be lengthened and adapted for retaining anchor 110 in a loaded position. Applicator 30 of FIG. 6 may be further modified for use with anchor 110 by eliminating outer tube 42, which has a primary function of shielding the penetrating tip of the needle.

Anchor 110 is an exemplary embodiment of a self-shielding anchor. Those skilled in the art will appreciate that numerous other embodiments are possible, including a self-shielding anchor that is unitarily formed from a biocompatible material by an injection molding process.

All of the suture anchor aspects described herein and their equivalents, may be subjected to a secondary manufacturing process such as tumbling, bead blasting or electropolishing to remove sharp burrs or edges that may injure tissue or inhibit proper deployment into tissue. In addition, all of the suture anchor aspects may be coated with a second material in order to provide desirable properties that may facilitate the deployment of the anchor and/or improve the surgical outcome. For example, the suture anchor may be coated with a lubricious coating, a polymeric coating, a drug-releasing coating, an anti-bacterial coating or a colored coating to facilitate identification.

Suture Anchor Applicator

Figure 18A:
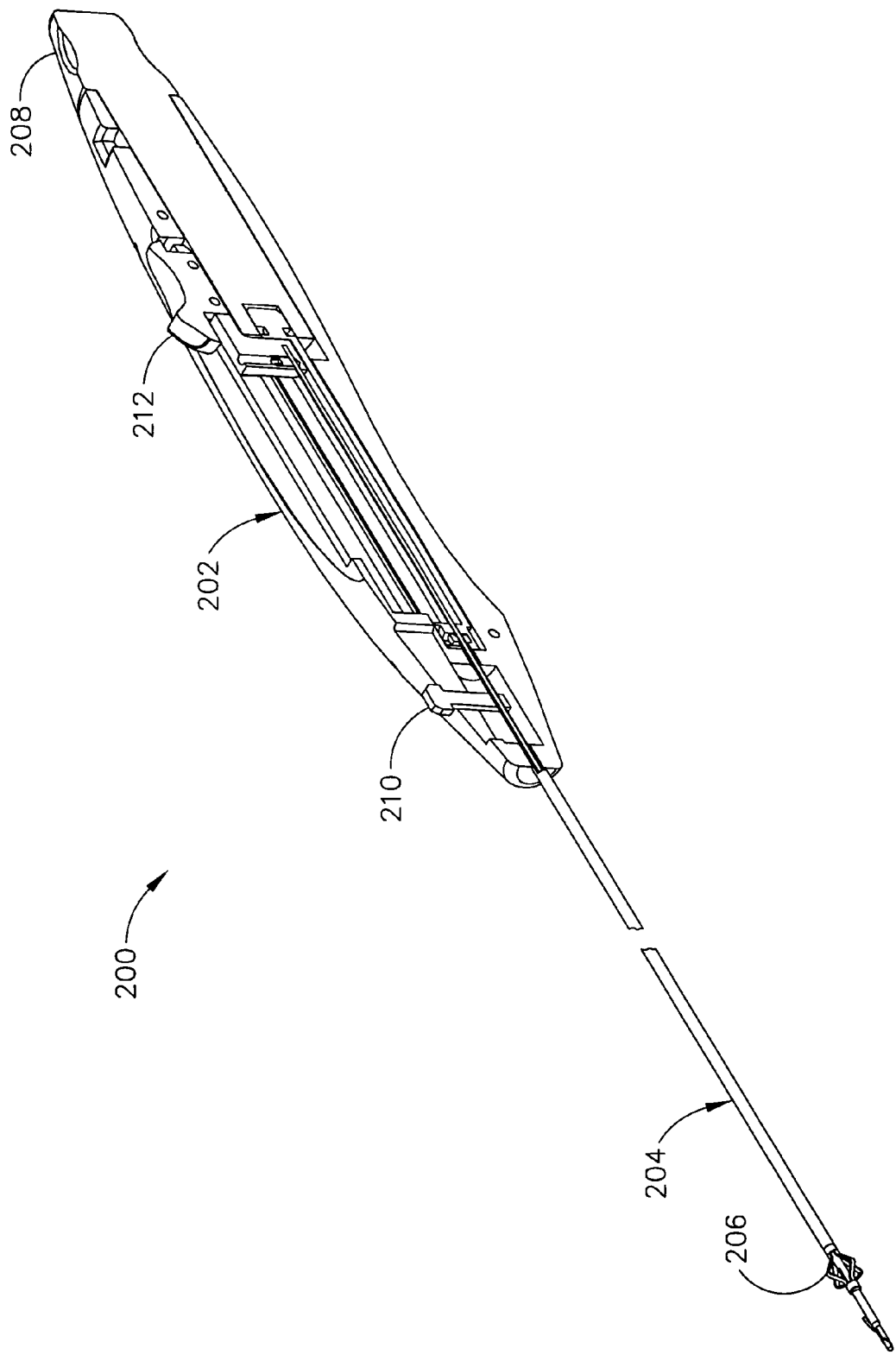
FIG. 18A is a perspective view of a second embodiment of a suture anchor applicator, including a sectional view of a handle.
Figure 18B:
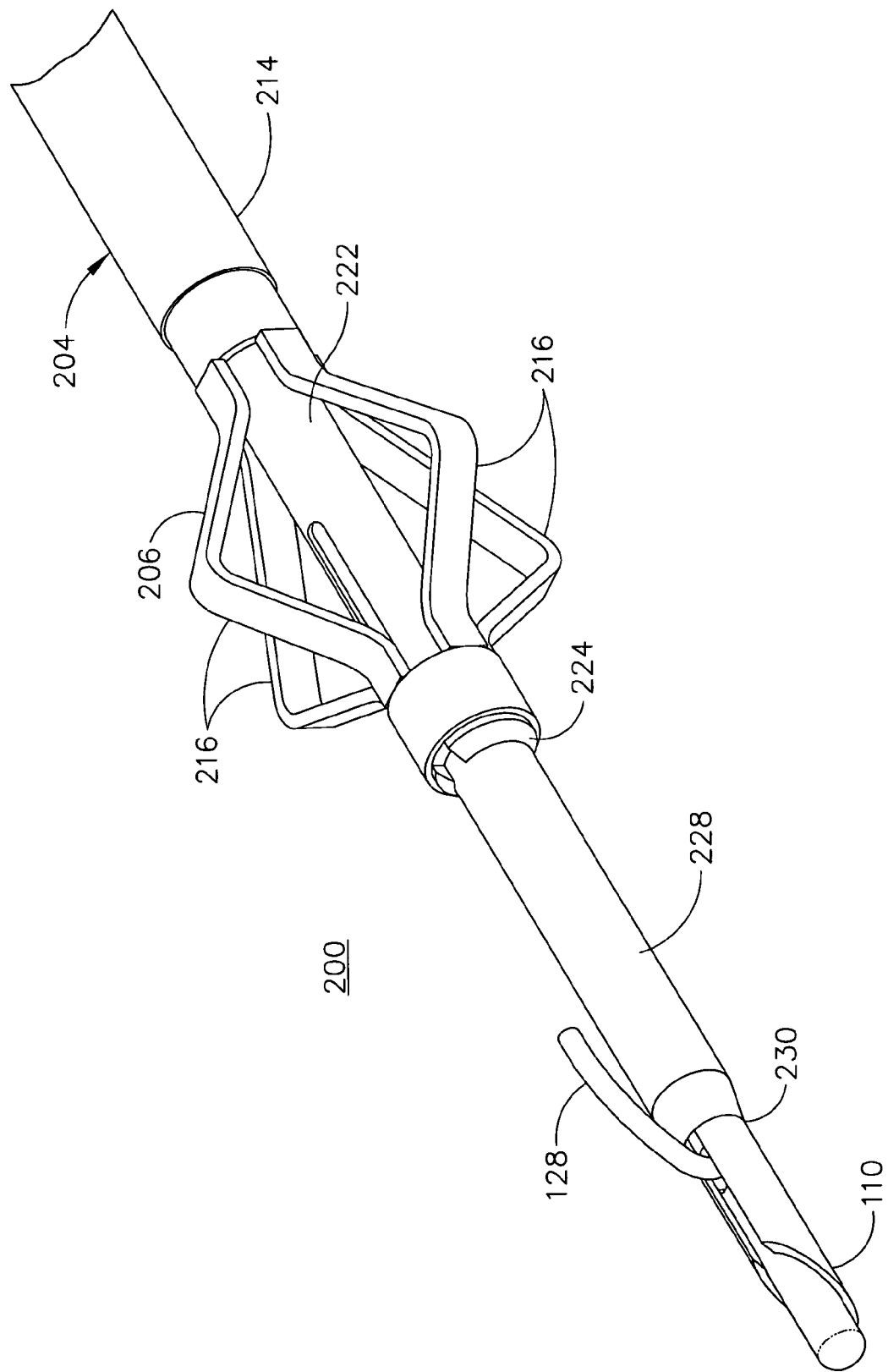
FIG. 18B is a perspective view of the distal portion of the applicator shown in FIG. 18A, including a tissue stop shown in an expanded configuration.

FIG. 18A is a perspective view of a second embodiment of a suture anchor applicator (also referred to as a medical instrument), generally designated 200, that is adapted to help prevent injury to nearby anatomical structures while deploying a suture anchor. FIG. 18B is a perspective view of the distal portion of applicator 200, shown with suture anchor 110 of FIG. 16. Applicator 200 may include an elongated shaft 204 attached to a handle 202. Applicator 200 may be similar to applicator 30 of FIG. 6. However, applicator 200 may also include a tissue stop 206 near the distal end of shaft 204. Tissue stop 206 can function to control the penetration depth of the distal end of the instrument into tissue to help prevent accidental injury to tissue/organs on the distal, "blind" side of the tissue being intentionally penetrated. Tissue stop 206 may also provide a visual indication of the needle penetration depth, as viewed through the endoscope. Applicator 200 is described next as it may be adapted for use with suture anchor 110 of FIG. 16, although applicator 200 may also be adapted for use with many types of suture anchors, including any of the suture anchor aspects described herein and their equivalents.

As may be seen in FIG. 18A, handle 202 may include a first actuator 208, a second actuator 210 and a third actuator 212. A physician may operate first actuator 208 to set the distance between the distal end of applicator 200 and tissue stop 206, thereby helping to control the penetration depth of the distal end into tissue. A physician may operate second actuator 210 to change tissue stop 206 between a collapsed and an expanded configuration. A physician may operate third actuator 212 to deploy suture anchor 110 into tissue, thereby attaching suture 128 to the tissue.

FIG. 18B shows tissue stop 206 in the expanded configuration. FIGS. 19 and 20 are longitudinal sectional views of the distal portion of applicator 200. FIG. 19 shows tissue stop 206 in the collapsed configuration and FIG. 20 shows tissue stop 206 in the expanded configuration. The distal and proximal ends of shaft 204 define a longitudinal axis 240. Axis 240 may be curvilinear if shaft 204 is adapted for use with a flexible endoscope. Shaft 204 may include an inner tube 228 having a channel 229 extending therethrough and slidably retaining an actuating element 226. The proximal end of inner tube 228 may be attached to handle 202. The proximal end of actuating element 110 may be operatively connected to third actuator 212 of handle 202. The distal end of actuating element 226 may be operatively engaged with anchor 110, which is shown positioned inside channel 229 in a loaded position and partially extending from a tapered distal end 230 of inner tube 228. Suture 128 may be draped alongside shaft 204 for insertion into the working channel of a flexible endoscope. When a physician operates third actuator 212, actuating element 226 may forcibly eject suture anchor 110 from inner tube 226.

An intermediate tube 222 may be movably and coaxially retained over inner tube 228. The distal end of intermediate tube 222 may include a radial flange 224. The proximal end of intermediate tube 222 may be operatively engaged to first actuator 208. The physician may operate first actuator 208 to move intermediate tube 222 between an extended position, in which flange 224 is distal to penetrating tip 114 of anchor 110, and a retracted position, in which flange 224 is proximal to tapered end 230 of inner tube 228. First actuator 208 may be provided with calibrations or a visual indicator such that the physician may position and hold intermediate tube 222 in any longitudinal position between the extended and retracted positions and know the maximum penetration depth of inner tube 228.

Still referring to FIGS. 19 and 20, an outer tube 214 (also referred to as a force element) may be movably and coaxially retained over intermediate tube 222. The proximal end of outer tube 214 may be operatively connected to second actuator 210. The distal end of outer tube 214 may be attached or unitarily formed with a proximal stop ring 220 of tissue stop 206, which may also be coaxially retained on intermediate tube 222.

Figure 24:
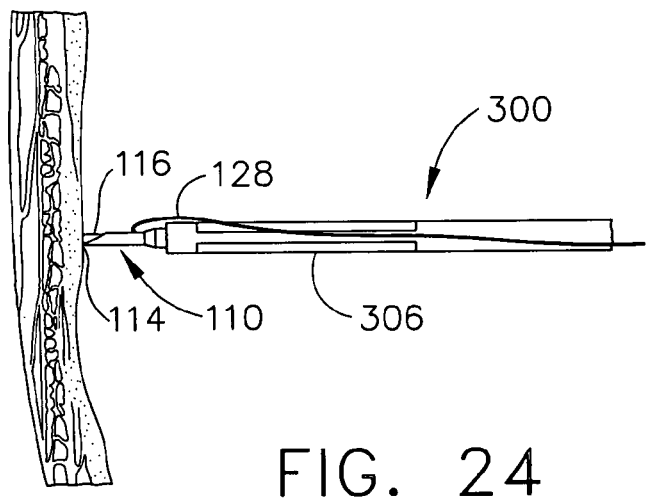

Tissue stop 206 may be formed such as by injection molding from a biocompatible polymer or metal. Tissue stop 206 may include at least one arm 216 that is approximately parallel to the longitudinal axis 240 when tissue stop 206 is in the collapsed configuration for easy passage through the working channel of an endoscope. Arm 216 may extend outwardly from longitudinal axis 240 when tissue stop 206 is in the expanded configuration, such that only the portion of applicator 200 distal to tissue stop 206 may penetrate tissue. As shown in FIG. 18B, tissue stop 206 may have four arms 216 positioned around axis 240. The distal end of each arm may be attached to a distal stop ring 218 and the proximal end of each arm may be attached to the proximal stop ring 220. Distal stop ring 218 may be fixed to intermediate tube 222 and proximal stop ring 220 may be slidably retained on intermediate tube 222 between flange 224 and outer tube 214. When the physician moves second actuator 210 in the distal direction, outer tube 214 can force tissue stop 206 against flange 224 and cause arms 216 to buckle as shown in FIG. 24 into the expanded configuration. The physician may move second actuator 210 proximally to change tissue stop 206 back to the collapsed configuration in order to remove applicator 200 from the endoscope.

It would also be possible for proximal stop ring 220 to be fixed to intermediate tube 222 and distal stop ring 218 to be slidably retained on intermediate tube 222. Instead of outer tube 214, another type of force element, such as a wire (not shown) may be connected to distal ring 218 and extended through channel 229 to handle 202. The proximal end of the wire force element could be connected to second actuator 210. The physician could then move second actuator 210 in the proximal direction to change tissue stop 206 from the collapsed to the expanded configuration.

The longitudinal position of flange 224 may set a distance "D2" (FIG. 24) between tissue stop 206 and tapered distal end 230. Penetrating tip 114 of anchor 110 may extend a distance "D1" distal to tapered distal tip 230. A maximum penetration depth of tip 114, therefore, is approximately equal to D1+D2, which may be visually indicated by calibrations (not shown) on first actuator 208.

An alternate embodiment of applicator 200 may include a tissue stop that is formed from a spring material such that the tissue stop is in the expanded configuration when unconstrained. In such an alternate embodiment, the tissue stop may be attached to the distal end of an intermediate tube that the physician may move to any longitudinal position between an extended and a retracted position. An outer sheath may be provided on the shaft of the applicator such that the physician may move the sheath distally to slide over and collapse the tissue stop and may move the sheath proximally to uncover the tissue stop and allow it to expand. Calibrations may be provided on the actuator such that the physician can know the maximal penetration depth of the tip.

Figure 21:
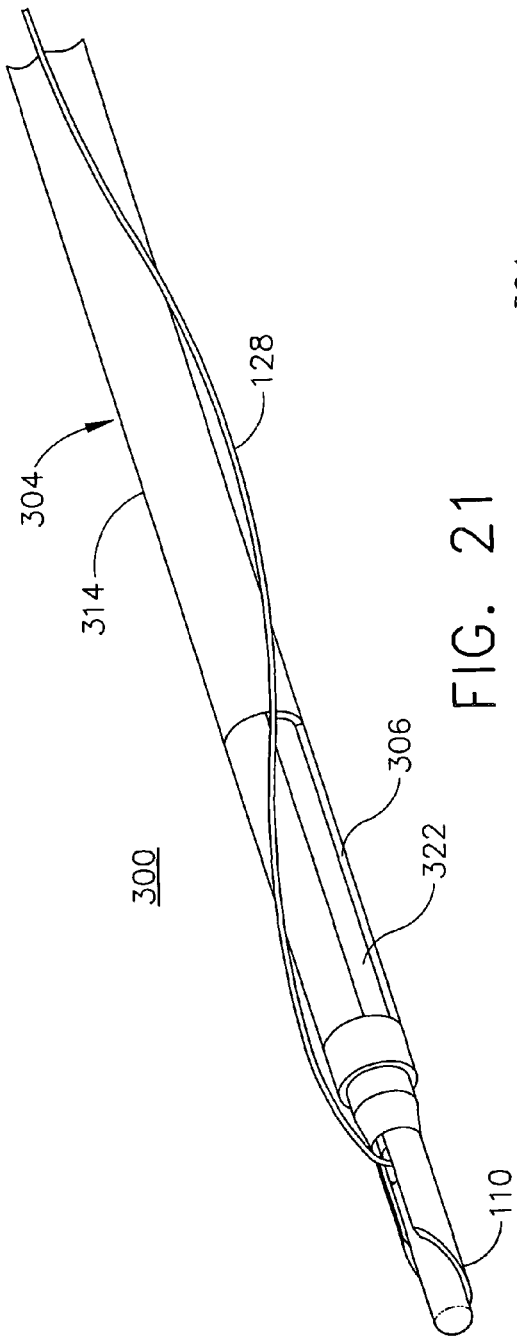
FIG. 21 is a perspective view of the distal portion of a third embodiment of a suture anchor applicator, including a second aspect of a tissue stop shown in a collapsed configuration.
Figure 22:
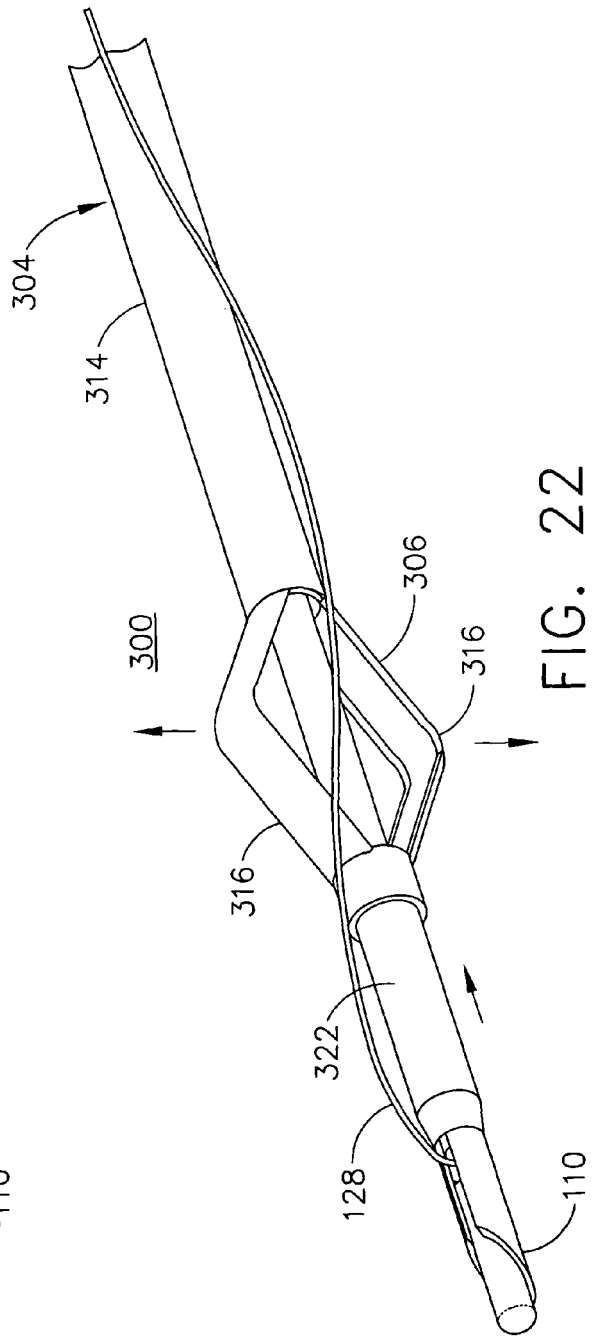
FIG. 22 is a perspective view of the distal portion of the applicator shown in FIG. 21, showing the tissue stop in an expanded configuration.

FIG. 21 is a perspective view of the distal portion of a third embodiment of a suture anchor applicator, generally designated 300, and showing anchor 110 (FIG. 16) having suture 128 in a loaded position in the distal end of an inner tube 322 of a shaft 304. Applicator 300 may include a tissue stop 306 that is shown in a collapsed configuration in FIG. 21 and in an expanded configuration in FIG. 22. Tissue stop 306 may have a pair of arms 316 that may be unitarily formed with a polymeric sheath 314 covering inner tube 322. Arms 316 may be formed to be in the expanded configuration when unconstrained, such that it is necessary for the user to collapse arms 316 as the distal end of applicator 300 is inserted into the proximal opening of the working channel or auxiliary passageway of the endoscope. When tissue stop 306 emerges from the distal opening of the working channel of the endoscope, arms 316 automatically spring outwardly, at least partially. When the physician advances applicator 300 in the distal direction such that tissue stop 306 bears against the tissue being penetrated by anchor 110 and inner tube 322, arms 316 further expand (if not already fully expanded) to the expanded configuration, thereby setting a maximum penetration depth of anchor 110 and inner tube 322 into the tissue. Withdrawal of applicator 300 through the working channel of the endoscope forces tissue stop 306 back into the collapsed configuration. Therefore, an outer sheath, such as sheath 214 of applicator 200 shown in FIG. 18B, is not required for applicator 300 in FIG. 21 to change tissue stop 306 between the collapsed and expanded configurations.

FIGS. 23-28 illustrate applicator 300 of FIG. 21 being used to attach anchor 110 to the tissue of a patient. For clarity, the endoscope used to provide access and visualization to the tissue is not shown, but it should be understood that the distal end of the endoscope may also be near and directed towards the tissue to be penetrated by anchor 110.

Figure 23:
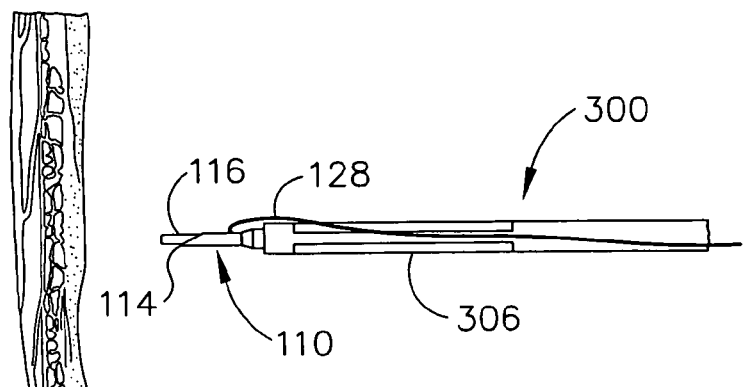
Figure 25:
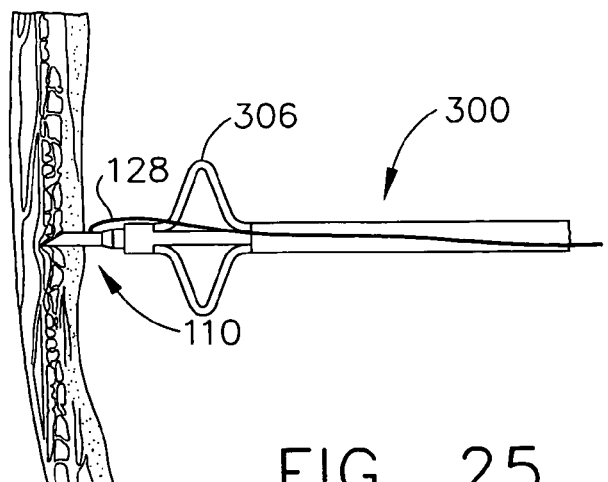
Figure 26:
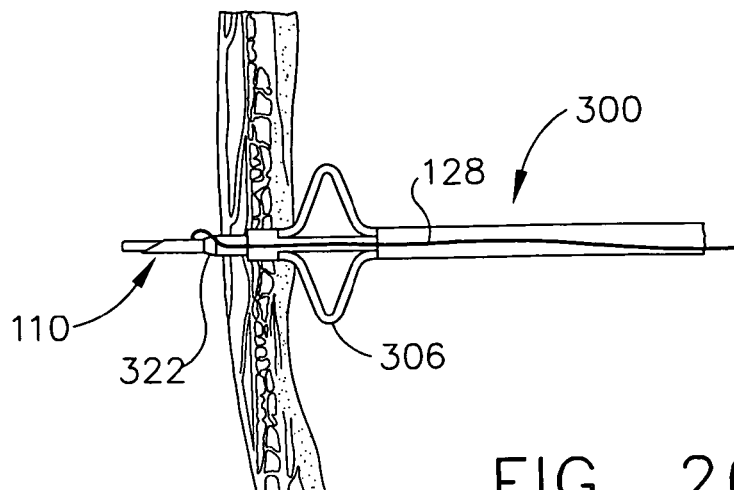
Figure 27:
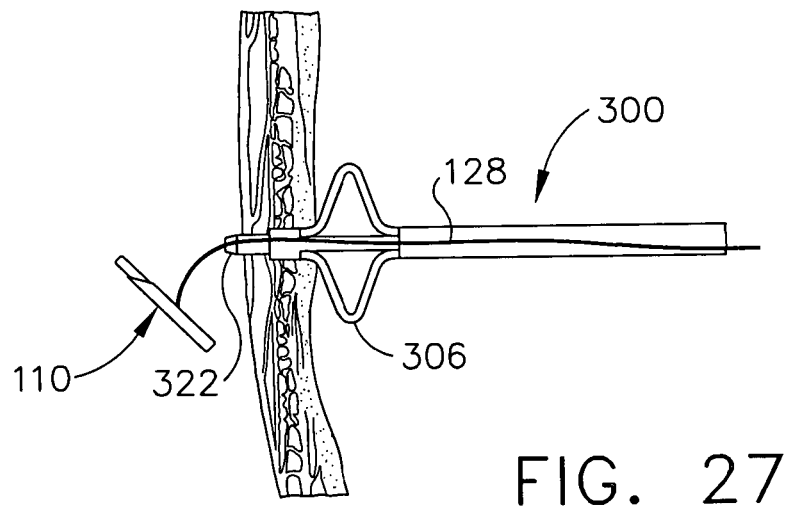
Figure 28:
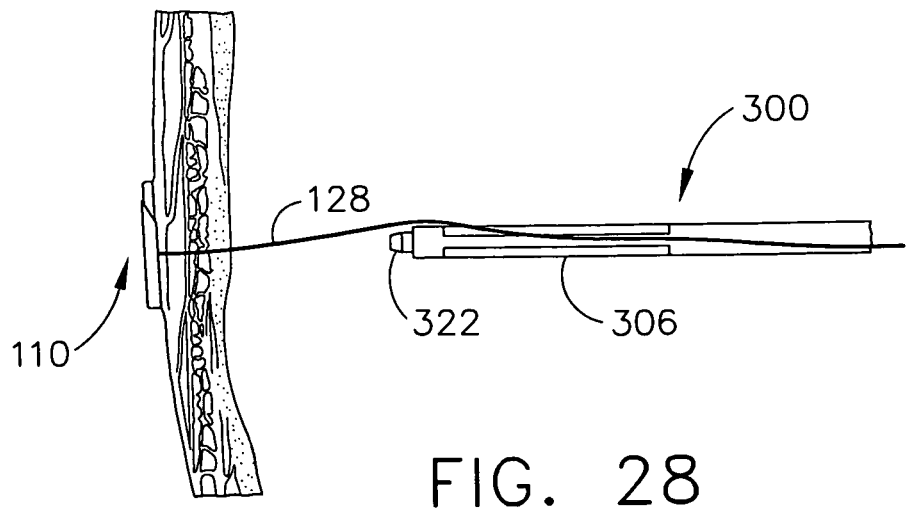

In FIG. 23, the distal end of applicator 300 containing anchor 110 is positioned near the tissue layers (e.g., stomach wall). Tissue stop 306 is shown in the collapsed configuration, as it would be when positioned inside of the working channel of the endoscope. FIG. 24 shows shielding element 116 partially retracted and penetrating tip 114 of anchor 110 beginning to pierce into the tissue as the user slowly pushes on the proximal end of applicator 300. FIG. 25 shows shielding element 116 fully retracted into anchor 110 as penetrating tip 114 penetrates the tissue layers. FIG. 26 shows anchor 110 and the distal end of inner tube 322 penetrated through the tissue layers and entering the body cavity distal to the penetrated tissue layers. Tissue stop 306 is shown as it is pushed against the tissue layers and in the fully expanded configuration, thereby limiting the maximal penetration depth of anchor 110 and inner tube 322. Suture 128 is shown trailing proximally through the tissue opening created by penetrating tip 114. FIG. 27 shows anchor 110 deployed into the body cavity distal to the penetrated tissue layers and reorienting to resist pull-out from the tissue layers when a tensile force is applied to suture 128. FIG. 28 shows anchor 110 being drawn against the distal side of the penetrated tissue layers as a tensile force is lightly applied to suture 128. FIG. 28 also shows applicator 300 withdrawn from the tissue and into the working channel, thereby forcing tissue stop 306 to change to the collapsed configuration for removal from the endoscope.

A method of endoscopically attaching a suture anchor to the tissue of a patient may include the following: A suture anchor applicator, wherein the applicator includes a tissue stop movable between a collapsed and an expanded configuration and the applicator contains a suture anchor in a loaded position. The endoscopic portion of an endoscope is positioned in the patient to provide access and visualization of a wound in the tissue. While the tissue stop is in the collapsed configuration, the shaft of the applicator is introduced into the working channel of the endoscope. The distal end of the applicator is positioned near the tissue and the tissue stop is changed to the expanded configuration. The applicator is advanced distally such that the anchor and the distal end of the applicator penetrates into the tissue to approximately a maximal penetration depth as determined by the location of the tissue stop on the shaft of the applicator. The applicator is remotely actuated to deploy the suture anchor into the tissue, thereby attaching the suture anchor to the tissue with the suture attached thereto and extending through the penetrated tissue and the work channel. The applicator is withdrawn proximally through the working channel and removed from the endoscope.

Figure 29:
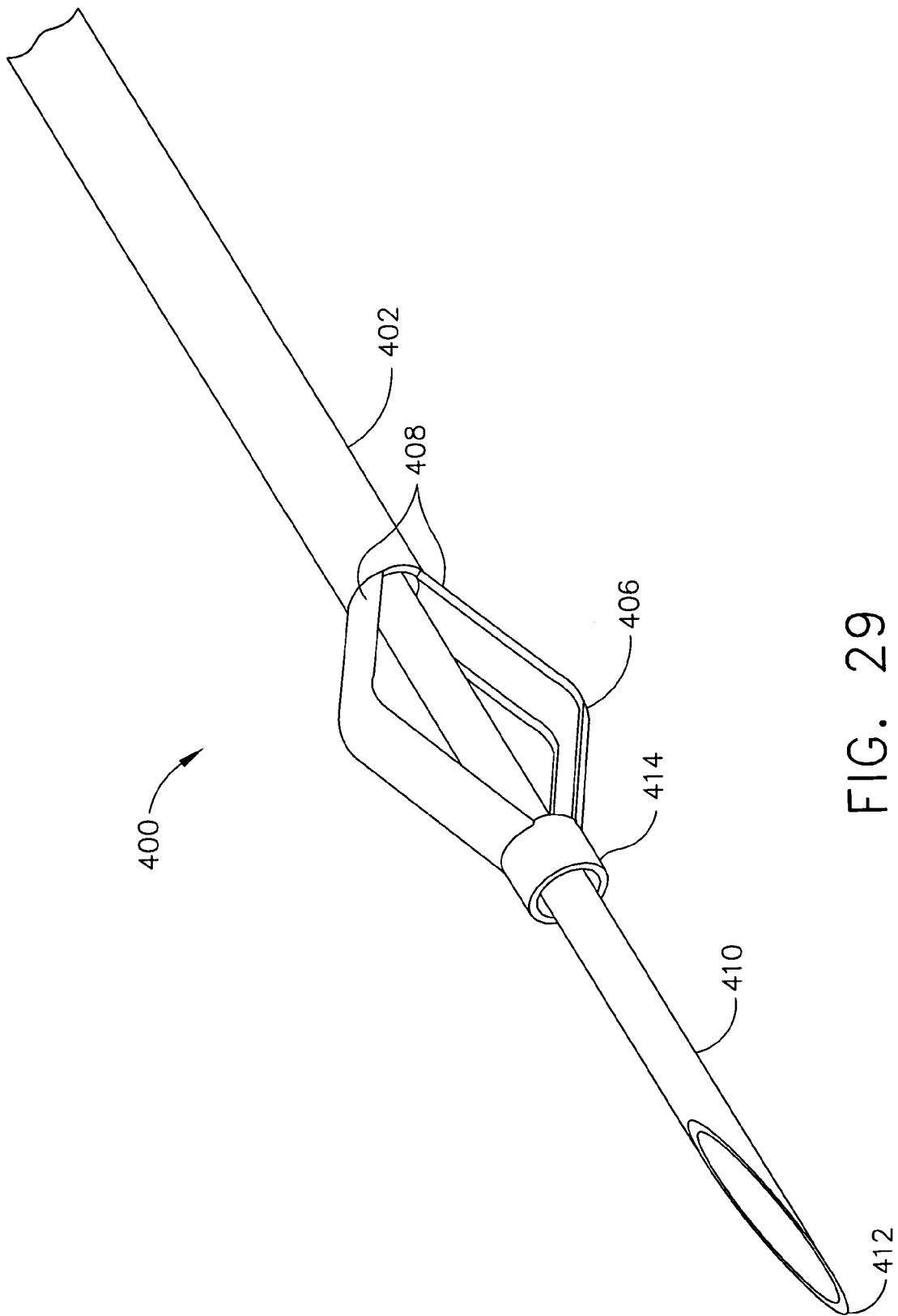
FIG. 29 is a perspective view of the distal portion of a fourth embodiment of a suture anchor applicator.

FIG. 29 is a perspective view of the distal portion of a fourth embodiment of a suture anchor applicator, generally designated 400, and also referred to as a medical instrument. Applicator 400 may include a tissue stop 406 (shown in an expanded configuration) having a pair of arms 408 that may be unitarily formed with a polymeric sheath 402 covering an inner tube 410. A sharp, penetrating tip 412 may be ground onto the distal end of inner tube 410 such that applicator 400 may be used with any of the suture anchors described herein. Arms 408 may be formed to be in the expanded configuration when unconstrained such that it is necessary for the user to collapse arms 408 as the distal end of applicator 400 is inserted into the proximal opening of the working channel of the endoscope. When tissue stop 406 emerges from the distal opening of the working channel of the endoscope, arms 408 automatically spring outwardly, at least partially. When the physician advances applicator 400 in the distal direction such that a distal end 414 of tissue stop 406 bears against the tissue being penetrated by inner tube 410, arms 408 may further expand (if not already fully expanded) to the expanded configuration, thereby setting a maximum penetration depth of inner tube 410 into the tissue. Withdrawal of applicator 400 through the working channel of the endoscope forces tissue stop 406 back into the collapsed configuration.

The proximal end of sheath 402 may be operatively connected to a control on a handle (not shown) such that the longitudinal position of sheath 402 relative to inner tube 410 may be adjustable by the user. Using this control, distal end 414 may be extended to a position distal to penetrating tip 412 while the distal end of applicator 400 is advanced to the wound site and retracted to a position proximal to tip 412 when it is desired to penetrate tissue. Calibrations and/or a visual indicator may be provided on the handle to indicate the position of distal end 414 such that the user may know the approximate penetration depth of inner tube 410 into the tissue.

Although various aspects of expandable suture anchors, self-shielding suture anchors, suture anchor applicators and methods have been shown and described, it should be understood that modifications may occur to those skilled in the art.

What is claimed is:

1. A self-shielding suture anchor comprising:
   a body having a proximal end and a distal end, the distal end defining a single pointed tip;
   a shielding element connected to, and received at least partially within, the body, the shielding element being movable relative to the distal end between a shielding position, wherein the shielding element is distal to the pointed tip, and a retracted position, wherein the shielding element is proximal to the pointed tip;
   a spring element operatively associated with the shielding element to bias the shielding element to the shielding position; and
   a surgical suture attached to the body and extending from the body between the proximal and distal ends; wherein the shielding element and spring element are adapted for the suture to be threaded therethrough such that the suture holds the shielding element and the spring element in operative association inside of the body.

2. The self-shielding suture anchor of claim 1, wherein the body is formed from a metallic tube.

3. The self-shielding suture anchor of claim 2, wherein the pointed tip is formed by grinding the distal end.

4. The self-shielding suture anchor of claim 1, wherein the shielding element includes a blunt end, the blunt end being distal to the pointed tip in the shielding position and proximal to the pointed tip in the retracted position.

5. The self-shielding suture anchor of claim 1, wherein the spring element is a compression spring.

6. The self-shielding suture anchor of claim 5, wherein the spring element is a metallic coil spring.

7. The self-shielding suture anchor of claim 1, wherein the suture extends from the body approximately half-way between the proximal and distal ends.

8. The self-shielding suture anchor of claim 1, wherein the suture is retainably attached to the body by a knot in the suture or a ferrule crimped onto the suture.

9. The self-shielding suture anchor of claim 1, wherein the suture is fixedly attached to the body by gluing, crimping, welding, insert molding or a mechanical attachment.

10. The self-shielding suture anchor of claim 1, wherein the suture is formed from a conventional surgical suture.

11. The self-shielding suture anchor of claim 1, wherein the suture is approximately 20-200 centimeters long.

12. The self-shielding suture anchor of claim 1, wherein at least a portion of the suture anchor is coated with at least one of a lubricious coating, a polymeric coating, a drug-releasing coating, an anti-bacterial coating and a colored coating.

13. The self-shielding suture anchor of claim 1 wherein the body defines a bore and a proximal end of the shielding element is slidably received within the bore.

14. A self-shielding suture anchor comprising:
a body having a proximal end and a distal end, the distal end including a penetrating tip, wherein the body defines a bore;
a shielding element having a blunt distal end and a proximal end opposite the blunt distal end, the proximal end being slidably received within the bore, the shielding element being movable relative to the distal end of the body between a shielding position and a retracted position, wherein the blunt end is distal to the penetrating tip in the shielding position and proximal to the penetrating tip in the retracted position;
a spring element operatively connected to the shielding element to bias the shielding element to the shielding position; and
a surgical suture attached to the body and extending from the body between the proximal and distal ends; wherein the shielding element and spring element are adapted for the suture to be threaded therethrough such that the suture holds the shielding element and the spring element in operative association inside of the body.

15. The self-shielding suture anchor of claim 14, wherein the suture extends from the body approximately half-way between the proximal and distal ends of the body.

16. The self-shielding suture anchor of claim 14, wherein the suture is retainably attached to the body by a knot in the suture or a ferrule crimped onto the suture.

17. The self-shielding suture anchor of claim 14 wherein the penetrating tip is shaped into a pointed tip.

* * * * *